US008858932B2

(12) United States Patent
Ghosh

(10) Patent No.: US 8,858,932 B2
(45) Date of Patent: Oct. 14, 2014

(54) REPAIR AND/OR RECONSTITUTION OF INVERTEBRAL DISCS

(75) Inventor: Peter Ghosh, Fairlight (AU)

(73) Assignee: Mesoblast, Inc., New York, NY (US)

( * ) Notice: Subject to any disclaimer, the term of this patent is extended or adjusted under 35 U.S.C. 154(b) by 0 days.

(21) Appl. No.: 13/000,721

(22) PCT Filed: Jun. 25, 2009

(86) PCT No.: PCT/AU2009/000817
§ 371 (c)(1),
(2), (4) Date: Apr. 1, 2011

(87) PCT Pub. No.: WO2009/155656
PCT Pub. Date: Dec. 30, 2009

(65) Prior Publication Data
US 2011/0189138 A1 Aug. 4, 2011

Related U.S. Application Data

(60) Provisional application No. 61/133,111, filed on Jun. 25, 2008.

(51) Int. Cl.
*A01N 63/00* (2006.01)

(52) U.S. Cl.
USPC ............................ 424/93.7; 435/374; 435/377

(58) Field of Classification Search
CPC ............ A61K 2300/00; A61K 31/726; A61K 31/727; A61K 31/728; A61K 2035/124; A61K 35/12; A61K 35/28; C12N 5/0663; C12N 2501/90; C12N 2501/905; A01N 1/02; A61L 2430/38; A61L 27/3834; A61L 27/3856; A61L 27/52
USPC .......................... 424/93.7, 469; 435/374, 377
See application file for complete search history.

(56) References Cited

U.S. PATENT DOCUMENTS

| 2003/0069639 A1 | 4/2003 | Sander et al. |
| 2010/0203020 A1 | 8/2010 | Ghosh |

FOREIGN PATENT DOCUMENTS

| AU | 2006200478 A1 | 2/2006 |
| WO | WO 97/18842 A1 | 5/1997 |
| WO | WO 01/35968 A1 | 5/2001 |
| WO | WO 01/80865 A2 | 11/2001 |
| WO | WO 02/070030 A1 | 9/2002 |
| WO | WO 2004/104166 A2 | 12/2004 |
| WO | WO 2005/082433 A1 | 9/2005 |
| WO | WO 2006/032092 A1 | 3/2006 |
| WO | WO 2006032075 A1 * | 3/2006 |
| WO | WO 2007/087519 A2 | 8/2007 |
| WO | WO 2007/136673 A2 | 11/2007 |
| WO | WO 2008/036374 A2 | 3/2008 |
| WO | WO 2008/073631 A2 | 6/2008 |
| WO | WO 2009/018613 A1 | 2/2009 |

OTHER PUBLICATIONS

Cruse, Julius. Lewis Robert; Illustrated Dictionary of Immunology; 1995 © CRC Press, Inc. ISBN 0-8493-4557-X (Appendix pp. 326).*
Sakai, Daisuke et. al; Transplantation of Mesenchymal Stem Cells Embedded in Atelocollagen gel to the Intervertebral Disc: A Potential Model for Disc Degeneration; Mar. 2003; Elsevier; Biomaterials 24 (2003) 3531-3541.*
Extended European Search Report issued Aug. 8, 2011 in connection with European Patent Application No. EP 09768629.9.
International Search Report issued by the International Searching Authority (ISA/AU) on Aug. 21, 2009 in connection with International Application No. PCT/AU2009/000817.
Written Opinion of the International Searching Authority issued by the International Searching Authority (ISA/AU) in connection with PCT International Application No. PCT/AU2009/000817.
International Preliminary Report on Patentability and Written Opinion of the International Searching Authority, issued by the International Searching Authority (ISA/AU) on Jan. 5, 2011 in connection with PCT International Application No. PCT/AU2009/000817.
Acosta et al., "The Potential Role of Mesenchymal Stem Cell Therapy for Intervertebral Disc Degeneration: A Critical Overview", Neurosurg. Focus, 2005, 19:1-6.
Herrera et al., "Exogenous Mesenchymal Stem Cells Localize to the Kidney by Means of CD44 Following Acute Tubular Injury", Kidney International, 2007, 72:430-441.
Liu et al., "Osteochondral Defect Repair with Autologous Bone Marrow-Derived Mesenchymal Stem Cells in an Injectable, In Situ, Cross-Linked Synthetic Extracellular Matrix", Tissue Engineering, 2006, 12:3405-3416.
Murphy et al., "Stem Cell Therapy in a Caprine Model of Osteoarthritis", Arthritis & Rheumatism, 2003, 48:3464-3474.
Otsuka et al., "Characterization of Osteoblastic Differentiation of Stromal Cell Line ST2 That is Induced by Absorbic Acid", Am. J. Physiol. (Cell Physiol.), 1999, 46:C132-C138.
Radice et al. "Hyaluronan-based Biopolymers as Delivery Vehicles for Bone-marrow-derived Mesechymal Progenitors", J. Biome. Res. Materials, Part A., 1999, 50:101-109.
Office Action issued Jul. 11, 2012 in connection with U.S. Appl. No. 12/452,767.
Office Action issued Sep. 18, 2012 in connection with U.S. Appl. No. 12/452,767.
Communication in Response to Sep. 18, 2012 Office Action filed Jan. 28, 2013 in connection with U.S. Appl. No. 12/452,767.
Nonfinal Office action issued Feb. 12, 2013 in connection with U.S. Appl. No. 12/452,767.
International Search Report issued by the International Searching Authority (ISA/AU) on Sep. 26, 2008 in connection with PCT International Application No. PCT/AU2008/001137.
Extended European Search Report issued Aug. 10, 2011 in connection with European Patent Application No. EP 08782887.7.
First Office Action issued Nov. 27, 2012 in connection with Australian Patent Application No. AU 2008286244.
First Office Action issued Dec. 16, 2011 in connection with Chinese Patent Application No. 200980124157.2.
Second Office Action issued Dec. 4, 2012 in connection with Chinese Patent Application No. 200980124157.2.

* cited by examiner

*Primary Examiner* — Susan Hanley
*Assistant Examiner* — Nghi Nguyen
(74) *Attorney, Agent, or Firm* — John P. White; Cooper & Dunham LLP

(57) ABSTRACT

This invention relates to a method for repair and reconstitution of invertebral discs in a subject which involves administration of STRO-1+ multipotent cells. The method of the invention is useful in the treatment of spinal conditions characterized by degeneration of the invertebral disc.

7 Claims, 23 Drawing Sheets

REPAIR AND/OR RECONSTITUTION OF INVERTEBRAL DISCS

This application is a §371 national stage of PCT International Application No. PCT/AU2009/000817, filed Jun. 25, 2009 and claims the benefit of U.S. Provisional Application No. 61/131,111, filed Jun. 25, 2008, the contents of each of which are hereby incorporated by reference into this application.

FIELD OF THE INVENTION

This invention relates to a method for repair and reconstitution of invertebral discs in a subject. The method of the invention is useful in the treatment of spinal conditions characterized by degeneration of the invertebral disc.

BACKGROUND OF THE INVENTION

The invertebral disc (IVD) is the largest predominantly avascular, aneural and alymphatic structure in the human body. The disc is critical for the normal function of the spinal column since it provides flexibility and mechanical stability during axial compression, flexion and extension. The IVD is composed of several specialised connective tissues: (i) the hyaline cartilage of the cartilaginous end plates (CEPs) which cover the surface of the vertebral bones (bodies) which are positioned above and below the disc; (ii) the fibrocartilagenous annulus fibrosus (AF) which encapsulates the nucleus pulposus (NP); and (iii) the central gelatinous nucleus pulposus (NP) which although it contains cartilage like cells is not a hyaline cartilage. A transitional zone (TZ) has also been identified which, as its name implies, is located between the AF and NP. The fibrocartilagenous AF is composed of concentric collagenous layers (lamellae) that are connected to the bony-rim of the vertebral bodies.

Proteoglycans (PGs) and types I, II, III, V, VI, IX, X, XI collagens are the major matrix components of all these disc tissues but their relative abundance and distribution is dependent on their anatomical locations. PGs, which have a high affinity for water molecules, are most abundant in the NP of "healthy discs". The water imbibed by the PGs generates a hydrostatic pressure within the NP that "inflates" the encapsulating fibrocartilagenous AF. It is the combination of these specialised connective tissues with their individual physio-chemical properties that contributes to the hydrodynamic and viscoelastic properties of the IVD that are essential for the normal biomechanical function of the spinal column.

The IVD undergoes profound matrix changes during ageing and degeneration. Studies of human cadaveric and disc specimens obtained at the time of spinal surgery have shown that discs from individuals in the middle to older age groups generally have a wide range of lesions (1, 2).

Three major types of disc lesions have been identified from these specimens: (i) the rim lesion, a transverse defect close to the attachment of the AF to the bone of the vertebral body rim; (ii) the concentric (circumferential) tear, where the annular lamellae separate from each other; and (iii) the radiating tear which results from the propagation of clefts initiating within the NP (1, 2, 3). Rim-lesions are of particular interest since they appear more commonly in adolescence and early adult life within the anterior region of the AF close to its insertion into the bone of the vertebral rim suggesting that they may be mechanically mediated. Their presence suggests early failure of the AF and is the primary cause of disc degeneration but studies on cadaveric specimens also indicate that other pathological features (concentric tears, cystic annular degeneration, dehydration of the NP, vertebral rim syndesmophytes and osteoarthritis of the posterior intervertebral joints) are also invariably present to some degree (1, 2). Although the temporal history of these respective disc lesions still remains the subject of debate it is generally agreed that loss of PGs and its associated water from the NP is an early etiological determinant of disc degeneration (4).

As already discussed the disc functions as a flexible hydro elastic cushion, largely mediated by the imbibition of water molecules within the NP. A decline in water content and thus swelling pressure of the NP would lead to the imposition of supraphysiological mechanical stresses on the AF resulting in localised failure.

Medical problems associated with back and neck-pain arising from disc degeneration are experienced by 90% of the population some time during their lives (5, 6). In man, back or neck pain of sufficient severity to warrant medical intervention increases in incidence in the third and fourth decades of life, peaks in the fifties and declines thereafter (5).

In the USA, back pain is the second most common reason for visit to a physician and medical conditions related to back and neck pain account for more hospitalisations than any other musculoskeletal disorder. Back pain is the primary cause of lost working hours. For example, in the United Kingdom it has been estimated that more than 11 million working days are lost annually from this complaint. Moreover, as the longevity of the population increases over the next few decades, back and neck pain problems are expected to increase accordingly.

Despite the high incidence and economic burden of neck and back pain in modern societies, the causes are still poorly understood. There is however general agreement that degeneration and/or failure if the IVD is the primary cause of pain, either directly from the nerves present in the outer AF or from the adjacent spinal structures that become mechanically compromised by the loss of disc hydroelastic function (7, 8, 9, 10). Disc disease is responsible for 23-40% of all cases of low back pain (11, 12). The outer AF is innervated and nerve fibres may extend as deeply as its inner third, thus any pathological changes to the outer AF may invoke pain (13, 14, 15).

The existing paradigm for treating back or neck pain of discal origin is empirical, directed either toward life-style changes or use of anti-inflammatory/analgesic drugs to minimise the symptomatology or to surgical intervention that may require resection of the degenerate tissues or spinal arthrodesis to restrict movement. Notwithstanding the widespread use of spinal fusion for the relief of neck or low back pain it is known that this is not a benign procedure since the mechanical stress imposed on adjacent discs by the introduction of the rigid segment across the disc space accelerates degenerate changes in adjacent discs which may become symptomatic at a later stage (16). Clearly alternative methods of treatment are required.

Intra-discal administration of the protein, osteogenic protein-1 (OP-1) (Bone morphogenetic protein-7), has been reported to stimulate disc matrix repair following experimentally produced degeneration. Disc degeneration was produced in rabbits by prior injection of the depolymerising enzyme chondroitinase ABC into the disc NP—the procedure being known as chemonucleolysis (17). Both NP and AF cells were found to be far more efficient at re-establishing a functional matrix after chemonucleolysis. Disc cells embedded in a normal dense extracellular matrix were found to be largely un-responsive to the stimulatory effects of OP-1 on PG synthesis (17).

Studies examining potential cellular therapies to achieve repair of degenerate canine and human IVDs using autologous chondrocytes have been reported (18, 19). The cells used were the chondrocytes harvested from healthy NP of the same species and subsequently re-implanted into the defect disc. The disadvantage of this approach is that the cells used for this purpose would need to be harvested from adjacent healthy discs or from other donors of the same species. Violation of the AF is required to obtain such cells and this process not only damages AF structure but also the removal of viable cells from the NP would accelerate degenerative changes in this tissue. Clearly this procedure would have limited human application.

SUMMARY OF THE INVENTION

The present application describes for the first time the in vivo use of STRO-1$^+$ multipotential cells to promote reconstitution of the nuclei pulposi and annuli fibrosi of degenerate intervertebral discs. The STRO-1$^+$ multipotential cells were derived form an allogeneic source and were well tolerated in the animal models used in this study. This suggests that the STRO-1$^+$ multipotential cells from donors can be grown in large numbers and developed as "off the shelf" products for the treatment of degenerate intervertebral discs.

Accordingly, the present invention provides a method for reconstituting and/or repairing an invertebral disc in a subject, the method comprising administering to the invertebral disc mesenchymal precursor cells (STRO-1$^+$ multipotential cells) and/or progeny cells thereof.

In an embodiment of the present invention, the STRO-1$^+$ multipotential cells and/or progeny cells thereof are administered into the nucleus pulposus of the invertebral disc.

Preferably, the STRO-1$^+$ multipotential cells are also TNAP$^+$, VCAM-1$^+$, THY-1$^+$, STRO-2$^+$, CD45$^+$, CD146$^+$, 3G5$^+$ or any combination thereof.

The STRO-1$^+$ multipotential cells and/or progeny cells thereof may be derived from an autogenic, allogeneic or xenogenic source. In one embodiment, the cells are derived from an allogeneic source.

The method of the present invention may also comprise administering a glycosaminoglycan (GAG), such as, for example, hyaluronic acid (hyaluronan) (HA), chondroitin sulfate, dermatan sulfate, keratan sulfate, heparin, heparin sulfate, to the invertebral disc. The GAG can be administered in the same or different composition as the STRO-1$^+$ multipotential cells and/or progeny cells thereof.

It will be appreciated that the method of the invention may be performed on any vertebrate. For example, the subject may be a mammal such as a human, dog, cat, horse, cow, or sheep.

The method of the present invention may be used in the treatment or prevention of spinal conditions characterized by degeneration of the intervertebral disc such as low back pain, age-related changes of the intervertebral disc or spondylolysis.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting Examples and with reference to the accompanying figures.

DETAILED DESCRIPTION OF PREFERRED EMBODIMENTS OF THE INVENTION

General Techniques and Selected Definitions

Figure 1:
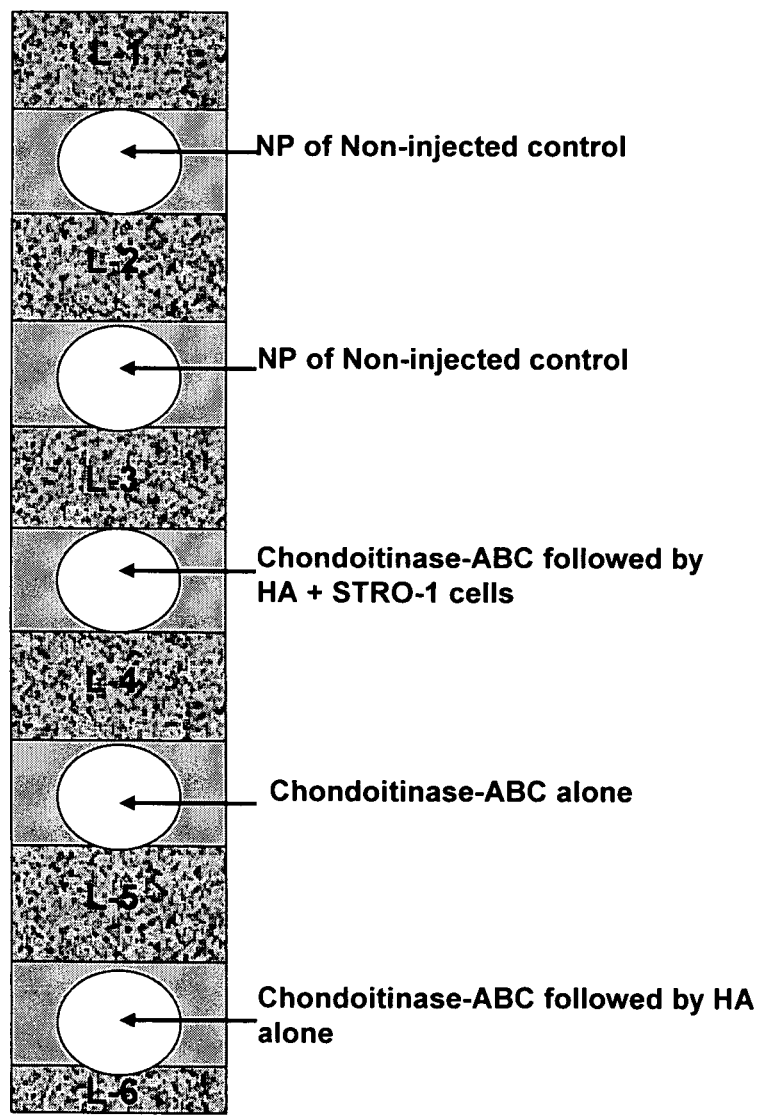
FIG. 1. Schematic representation of the lumber spinal levels treated with STRO-1 cells in all sheep Groups.

Unless specifically defined otherwise, all technical and scientific terms used herein shall be taken to have the same meaning as commonly understood by one of ordinary skill in the art (e.g., in cell culture, stem cell biology, molecular genetics, immunology, immunohistochemistry, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, CRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

As used herein, the terms "treating", "treat" or "treatment" include administering a therapeutically effective amount of STRO-1$^+$ multipotential cells and/or progeny cells thereof sufficient to reduce or eliminate at least one symptom of the specified condition.

As used herein, the terms "preventing", "prevent" or "prevention" include administering a therapeutically effective amount of STRO-1$^+$ multipotential cells and/or progeny cells thereof sufficient to stop or hinder the development of at least one symptom of the specified condition.

STRO-1$^+$ Multipotential Cells or Progeny Cells

As used herein, the phrase "STRO-1$^+$ multipotential cells" shall be taken to mean STRO-1$^+$ and/or TNAP$^+$ progenitor cells capable of forming multipotential cell colonies.

STRO-1$^+$ multipotential cells are cells found in bone marrow, blood, dental pulp cells, adipose tissue, skin, spleen, pancreas, brain, kidney, liver, heart, retina, brain, hair follicles, intestine, lung, lymph node, thymus, bone, ligament, tendon, skeletal muscle, dermis, and periosteum; and are capable of differentiating into germ lines such as mesoderm and/or endoderm and/or ectoderm. Thus, STRO-1$^+$ multipotential cells are capable of differentiating into a large number of cell types including, but not limited to, adipose, osseous, cartilaginous, elastic, muscular, and fibrous connective tissues. The specific lineage-commitment and differentiation pathway which these cells enter depends upon various influences from mechanical influences and/or endogenous bioactive factors, such as growth factors, cytokines, and/or local microenvironmental conditions established by host tissues. In one embodiment STRO-1$^+$ multipotential cells are non-hematopoietic progenitor cells which divide to yield daughter cells that are either stem cells or are precursor cells which in time will irreversibly differentiate to yield a phenotypic cell.

In another embodiment, the STRO-1$^+$ multipotential cells are enriched from a sample obtained from a subject, e.g., a subject to be treated or a related subject or an unrelated subject (whether of the same species or different). The terms 'enriched', 'enrichment' or variations thereof are used herein to describe a population of cells in which the proportion of one particular cell type or the proportion of a number of particular cell types is increased when compared with the untreated population.

In another embodiment, the cells used in the present invention express one or more markers individually or collectively selected from the group consisting of TNAP$^+$, VCAM-1$^+$, THY-1$^+$, STRO-2$^+$, CD45$^+$, CD146$^+$, 3G5$^+$ or any combination thereof.

By "individually" is meant that the invention encompasses the recited markers or groups of markers separately, and that, notwithstanding that individual markers or groups of markers may not be separately listed herein the accompanying claims may define such marker or groups of markers separately and divisibly from each other.

By "collectively" is meant that the invention encompasses any number or combination of the recited markers or groups of peptides, and that, notwithstanding that such numbers or combinations of markers or groups of markers may not be specifically listed herein the accompanying claims may define such combinations or sub-combinations separately and divisibly from any other combination of markers or groups of markers.

Preferably, the STRO-1$^+$ cells are STRO-1$^{bright}$ (syn. STRO-1$^{bri}$). Preferably, the STRO-1$^{bright}$ cells are additionally one or more of TNAP$^+$, VCAM-1$^+$, THY-1$^+$, STRO-2$^+$ and/or CD146$^+$.

In one embodiment, the STRO-1$^+$ multipotential cells are perivascular mesenchymal precursor cells as defined in WO 2004/85630.

A cell that is referred to as being "positive" for a given marker it may express either a low (lo or dim) or a high (bright, bri) level of that marker depending on the degree to which the marker is present on the cell surface, where the terms relate to intensity of fluorescence or other marker used in the sorting process of the cells. The distinction of lo (or dim or dull) and bri will be understood in the context of the marker used on a particular cell population being sorted. A cell that is referred to as being "negative" for a given marker is not necessarily completely absent from that cell. This terms means that the marker is expressed at a relatively very low level by that cell, and that it generates a very low signal when detectably labelled or is undetectable above background levels.

The term "bright", when used herein, refers to a marker on a cell surface that generates a relatively high signal when detectably labelled. Whilst not wishing to be limited by theory, it is proposed that "bright" cells express more of the target marker protein (for example the antigen recognised by STRO-1) than other cells in the sample. For instance, STRO-1$^{bri}$ cells produce a greater fluorescent signal, when labelled with a FITC-conjugated STRO-1 antibody as determined by fluorescence activated cell sorting (FACS) analysis, than non-bright cells (STRO-1$^{dull/dim}$). Preferably, "bright" cells constitute at least about 0.1% of the most brightly labelled bone marrow mononuclear cells contained in the starting sample. In other embodiments, "bright" cells constitute at least about 0.1%, at least about 0.5%, at least about 1%, at least about 1.5%, or at least about 2%, of the most brightly labelled bone marrow mononuclear cells contained in the starting sample. In a preferred embodiment, STRO-1$^{bright}$ cells have 2 log magnitude higher expression of STRO-1 surface expression relative to "background", namely cells that are STRO-1$^-$. By comparison, STRO-1$^{dim}$ and/or STRO-1$^{intermediate}$ cells have less than 2 log magnitude higher expression of STRO-1 surface expression, typically about 1 log or less than "background".

As used herein the term "TNAP" is intended to encompass all isoforms of tissue non-specific alkaline phosphatase. For example, the term encompasses the liver isoform (LAP), the bone isoform (BAP) and the kidney isoform (KAP). In a preferred embodiment, the TNAP is BAP. In a particularly preferred embodiment, TNAP as used herein refers to a molecule which can bind the STRO-3 antibody produced by the hybridoma cell line deposited with ATCC on 19 Dec. 2005 under the provisions of the Budapest Treaty under deposit accession number PTA-7282.

In one embodiment the STRO-1$^+$ multipotential cells are capable of giving rise to clonogenic CFU-F.

It is preferred that a significant proportion of the STRO-1$^+$ multipotential cells are capable of differentiation into at least two different germ lines. Non-limiting examples of the lineages to which the multipotential cells may be committed include bone precursor cells; hepatocyte progenitors, which are multipotent for bile duct epithelial cells and hepatocytes; neural restricted cells, which can generate glial cell precursors that progress to oligodendrocytes and astrocytes; neuronal precursors that progress to neurons; precursors for cardiac muscle and cardiomyocytes, glucose-responsive insulin secreting pancreatic beta cell lines. Other lineages include, but are not limited to, odontoblasts, dentin-producing cells and chondrocytes, and precursor cells of the following: retinal pigment epithelial cells, fibroblasts, skin cells such as keratinocytes, dendritic cells, hair follicle cells, renal duct epithelial cells, smooth and skeletal muscle cells, testicular progenitors, vascular endothelial cells, tendon, ligament, cartilage, adipocyte, fibroblast, marrow stroma, cardiac muscle, smooth muscle, skeletal muscle, pericyte, vascular, epithelial, glial, neuronal, astrocyte and oligodendrocyte cells.

In another embodiment, the STRO-1$^+$ multipotential cells are not capable of giving rise, upon culturing, to hematopoietic cells.

In one embodiment, the cells are taken from the subject to be treated, cultured in vitro using standard techniques and used to obtain supernatant or soluble factors or expanded cells for administration to the subject as an autologous or allogeneic composition. In an alternative embodiment, cells of one or more of the established human cell lines are used. In another useful embodiment of the invention, cells of a non-human animal (or if the patient is not a human, from another species) are used.

The present invention also contemplates use of supernatant or soluble factors obtained or derived from STRO-1$^+$ multipotential cells and/or progeny cells thereof (the latter also being referred to as expanded cells) which are produced from in vitro culture. Expanded cells of the invention may a have a wide variety of phenotypes depending on the culture conditions (including the number and/or type of stimulatory factors in the culture medium), the number of passages and the like. In certain embodiments, the progeny cells are obtained after about 2, about 3, about 4, about 5, about 6, about 7, about 8, about 9, or about 10 passages from the parental population. However, the progeny cells may be obtained after any number of passages from the parental population.

The progeny cells may be obtained by culturing in any suitable medium. The term "medium", as used in reference to a cell culture, includes the components of the environment surrounding the cells. Media may be solid, liquid, gaseous or a mixture of phases and materials. Media include liquid growth media as well as liquid media that do not sustain cell growth. Media also include gelatinous media such as agar, agarose, gelatin and collagen matrices. Exemplary gaseous media include the gaseous phase that cells growing on a petri dish or other solid or semisolid support are exposed to. The term "medium" also refers to material that is intended for use in a cell culture, even if it has not yet been contacted with cells. In other words, a nutrient rich liquid prepared for bacterial culture is a medium. A powder mixture that when mixed with water or other liquid becomes suitable for cell culture may be termed a "powdered medium".

In an embodiment, progeny cells useful for the methods of the invention are obtained by isolating TNAP$^+$ STRO-1$^+$ multipotential cells from bone marrow using magnetic beads labelled with the STRO-3 antibody, and then culture expanding the isolated cells (see Gronthos et al. *Blood* 85: 929-940, 1995 for an example of suitable culturing conditions).

In one embodiment, such expanded cells (progeny) (preferably, at least after 5 passages) can be TNAP$^-$, CC9$^+$, HLA class I$^+$, HLA class II$^-$, CD14$^-$, CD19$^-$, CD3$^-$, CD11a$^-$c$^-$, CD31$^-$, CD86$^-$, CD34$^-$ and/or CD80$^-$. However, it is possible that under different culturing conditions to those described herein that the expression of different markers may vary. Also, whilst cells of these phenotypes may predominate in the expended cell population it does not mean that there is a minor proportion of the cells do not have this phenotype(s) (for example, a small percentage of the expanded cells may be CC9$^-$). In one preferred embodiment, expanded cells still have the capacity to differentiate into different cell types.

In one embodiment, an expended cell population used to obtain supernatant or soluble factors, or cells per se, comprises cells wherein at least 25%, more preferably at least 50%, of the cells are CC9+.

In another embodiment, an expanded cell population used to obtain supernatant or soluble factors, or cells per se, comprises cells wherein at least 40%, more preferably at least 45%, of the cells are STRO-1$^+$.

In a further embodiment, the expanded cells may express one or more markers collectively or individually selected from the group consisting of LFA-3, THY-1, VCAM-1, ICAM-1, PECAM-1, P-selectin, L-selectin, 3G5, CD49a/CD49b/CD29, CD49c/CD29, CD49d/CD29, CD 90, CD29, CD18, CD61, integrin beta 6-19, thrombomodulin, CD10, CD13, SCF, PDGF-R, EGF-R, IGF1-R, NGF-R, FGF-R, Leptin-R (STRO-2=Leptin-R), RANKL, STRO-1$^{bright}$ and CD146 or any combination of these markers.

In one embodiment, the progeny cells are Multipotential Expanded STRO-1$^+$ Multipotential cells Progeny (MEMPs) as defined and/or described in WO 2006/032092. Methods for preparing enriched populations of STRO-1$^+$ multipotential cells from which progeny may be derived are described in WO 01/04268 and WO 2004/085630. In an in vitro context STRO-1$^+$ multipotential cells will rarely be present as an absolutely pure preparation and will generally be present with other cells that are tissue specific committed cells (TSCCs). WO 01/04268 refers to harvesting such cells from bone marrow at purity levels of about 0.1% to 90%. The population comprising STRO-1$^+$ multipotential cells from which progeny are derived may be directly harvested from a tissue source, or alternatively it may be a population that has already been expanded ex vivo.

For example, the progeny may be obtained from a harvested, unexpanded, population of substantially purified STRO-1$^+$ multipotential cells, comprising at least about 0.1, 1, 5, 10, 20, 30, 40, 50, 60, 70, 80 or 95% of total cells of the population in which they are present. This level may be achieved, for example, by selecting for cells that are positive for at least one marker individually or collectively selected from the group consisting of TNAP. STRO-1$^{bright}$, 3G5$^+$, VCAM-1, THY-1, CD146 and STRO-2.

MEMPS can be distinguished from freshly harvested STRO-1$^+$ multipotential cells in that they are positive for the marker STRO-1$^{bri}$ and negative for the marker Alkaline phosphatase (ALP). In contrast, freshly isolated STRO-1$^+$ multipotential cells are positive for both STRO-1$^{bri}$ and ALP. In a preferred embodiment of the present invention, at least 15%, 20%, 30%, 40%, 50%, 60%, 70%, 80%, 90% or 95% of the administered cells have the phenotype STRO-1$^{bri}$, ALP$^-$. In a further preferred embodiment the MEMPS are positive for one or more of the markers Ki67, CD44 and/or CD49c/CD29, VLA-3, α3β1. In yet a further preferred embodiment the MEMPs do not exhibit TERT activity and/or are negative for the marker CD18.

The STRO-1+ multipotential cell starting population may be derived from any one or more tissue types set out in WO 01/04268 or WO 2004/085630, namely bone marrow, dental pulp cells, adipose tissue and skin, or perhaps more broadly from adipose tissue, teeth, dental pulp, skin, liver, kidney, heart, retina, brain, hair follicles, intestine, lung, spleen, lymph node, thymus, pancreas, bone, ligament, bone marrow, tendon and skeletal muscle.

It will be understood that in performing the present invention, separation of cells carrying any given cell surface marker can be effected by a number of different methods, however, preferred methods rely upon binding a binding agent (e.g., an antibody or antigen binding fragment thereof) to the marker concerned followed by a separation of those that exhibit binding, being either high level binding, or low level binding or no binding. The most convenient binding agents are antibodies or antibody-based molecules, preferably being monoclonal antibodies or based on monoclonal antibodies because of the specificity of these latter agents. Antibodies can be used for both steps, however other agents might also be used, thus ligands for these markers may also be employed to enrich for cells carrying them, or lacking them.

The antibodies or ligands may be attached to a solid support to allow for a crude separation. The separation techniques preferably maximise the retention of viability of the fraction to be collected, Various techniques of different efficacy may be employed to obtain relatively crude separations. The particular technique employed will depend upon efficiency of separation, associated cytotoxicity, ease and speed of performance, and necessity for sophisticated equipment and/or technical skill. Procedures for separation may include, but are not limited to, magnetic separation, using antibody-coated magnetic beads, affinity chromatography and "panning" with antibody attached to a solid matrix. Techniques providing accurate separation include but are not limited to FACS. Methods for performing FACS will be apparent to the skilled artisan.

Antibodies against each of the markers described herein are commercially available (e.g., monoclonal antibodies against STRO-1 are commercially available from R&D Systems, USA), available from ATCC or other depositary organization and/or can be produced using art recognized techniques.

It is preferred that the method for isolating STRO-1+ multipotential cells, for example, comprises a first step being a solid phase sorting step utilising for example magnetic activated cell sorting (MACS) recognising high level expression of STRO-1. A second sorting step can then follow, should that be desired, to result in a higher level of precursor cell expression as described in patent specification WO 01/14268. This second sorting step might involve the use of two or more markers.

The method obtaining STRO-1+ multipotential cells might also include the harvesting of a source of the cells before the first enrichment step using known techniques. Thus the tissue will be surgically removed. Cells comprising the source tissue will then be separated into a so called single cells suspension. This separation may be achieved by physical and or enzymatic means.

Once a suitable STRO-1+ multipotential cell population has been obtained, it may be cultured or expanded by any suitable means to obtain MEMPs.

In one embodiment, the cells are taken from the subject to be treated, cultured in vitro using standard techniques and used to obtain supernatant or soluble factors or expanded cells for administration to the subject as an autologous or allogeneic composition. In an alternative embodiment, cells of one or more of the established human cell lines are used to obtain the supernatant or soluble factors. In another useful embodiment of the invention, cells of a non-human animal (or if the patient is not a human, from another species) are used to obtain supernatant or soluble factors.

The invention can be practised using cells from any non-human animal species, including but not limited to non-human primate cells, ungulate, canine, feline, lagomorph, rodent, avian, and fish cells. Primate cells with which the invention may be performed include but are not limited to cells of chimpanzees, baboons, cynomolgus monkeys, and any other New or Old World monkeys. Ungulate cells with which the invention may be performed include but are not limited to cells of bovines, porcines, ovines, caprines, equines, buffalo and bison. Rodent cells with which the invention may be performed include but are not limited to mouse, rat, guinea pig, hamster and gerbil cells. Examples of lagomorph species with which the invention may be performed include domesticated rabbits, jack rabbits, hares, cottontails, snowshoe rabbits, and pikas. Chickens (*Gallus gallus*) are an example of an avian species with which the invention may be performed.

Cells useful for the methods of the invention may be stored before use, or before obtaining the supernatant or soluble factors. Methods and protocols for preserving and storing of eukaryotic cells, and in particular mammalian cells, are known in the art (cf., for example, Pollard, J. W. and Walker, J. M. (1997) Basic Cell Culture Protocols, Second Edition, Humana Press, Totowa, N.J.; Freshney, R. I. (2000) Culture of Animal Cells, Fourth Edition, Wiley-Liss, Hoboken, N.J.). Any method maintaining the biological activity of the isolated stem cells such as mesenchymal stem/progenitor cells, or progeny thereof, may be utilized in connection with the present invention. In one preferred embodiment, the cells are maintained and stored by using cryo-preservation.

Administration and Compositions

The dosage of STRO-1+ multipotential cells or progeny thereof to be administered may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage. "Dosage unit form" as used herein refers to physically discrete units suited as unitary dosages for subjects to be treated; each unit containing a predetermined quantity of active compound calculated to produce the desired therapeutic effect in association with the required pharmaceutical carrier.

In one example, the dosage of STRO-1+ multipotential cells administered is in the range of 0.1 to $4.0 \times 10^6$ cells. The dosage may be, for example, $0.5 \times 10^6$ cells.

It is to be appreciated that the STRO-1+ multipotential cells and/or progeny thereof may be processed into various forms (e.g. solution suspension, solid, porous, woven, non-woven, particulate, gel, paste, etc.) before being added to the disc space.

Numerous biologic and synthetic materials are contemplated for co-injection with the STRO-1+ multipotential cells and/or progeny thereof into a nucleus pulposus to restore normal mechanical and or physiological properties to a damaged intervertbral disc. For example, one or more natural or synthetic glycosaminoglycans (GAGS) or mucopolysaccharides, such as, for example, hyaluronic acid (HA), chondroitan sulfate, dermatan sulfate, keratin sulfate, heparin, heparin sulfate, galactosaminoglycuronglycan sulfate (GGGS), see previous changes and others, including their physiological salts, may be injected directly into the nucleus pulposus. It has been suggested that HA plays a role in the stimulation of endogenous HA synthesis by synovial cells and proteoglycan synthesis by chondrocytes, inhibits the release of chondrodegradative enzymes, and acts as a scavenger of oxygen free radicals known to play part in cartilage deterioration. Chondroitin sulfate and glucosamine injectables have similarly been shown to block the progression of articular cartilage degeneration. Arguably, other GAG's may provide similar protective or restorative properties having therapeutic value making them ideal candidates for injection into a disc undergoing degenerative disc disease. Another valuable property of GAG's is their strong ability to attract and retain water. Thus, it may be appropriate to mix GAG's with water or other aqueous materials to form a viscous gel that may then be injected into the space created from aspiration of a nucleus pulposus, or alternatively, added to an existing nucleus pulposus as a supplement. Natural "hydrogels" can thereby be formed which are capable of filling space in three dimensions and acting like packing materials that resist crushing and enable a disc to adequately absorb the shock associated with movement.

Synthetic hyaluronic gels such as, for example, Euflexxa®, (Ferring Pharmaceuticals) or Restylane®. (Q-Med Aktiebolag Co., Sweden) are suitable for use in the present invention.

Examples of other injectable synthetic materials that may be used for co-administration include medical wade silicone, Bioplastique®. (solid silicone particles suspended in polyvinylpyrrolidone carrier; Uroplasty BV, Netherlands), Arteplast® (microspheres of polymethylmethacrylate (PMMA) suspended in gelatin carrier; Artcs Medical, USA), Artecoll® (smooth PMMA spheres suspended in bovine cartilage carrier; Artepharma Pharmazeu Tische, GMBH Co., Germany). Further, synthetic hydrogel compositions may be employed as a filler material to restore normal shape to a disc, thereby restoring normal bio-mechanical functions.

Antioxidants having known chondroprotective abilities are also candidates for injection into the nucleus pulposus. Examples of these include tocophereol (vitamin E), superoxide dismutase (SOD), ascorbate (vitamin C), catalase and others. Further, amphiphilic derivatives of sodium alginate and the like are also contemplated herein for injection. Additionally recombinant osteogenic protein-1 (OP-1) is a good candidate for injection because of its ability to promote the formation of a proteoglycan rich matrix by nucleus pulposus and annulus fibrosus cells.

Use of synthetic injectables is also contemplated. These are particularly applicable to situations where the primary goal is to restore bio-mechanical function to a disc. Hyaluronic acid alone or in combination with other glycosaminoglycans may be used as a carrier to deliver a biologically active material. In a preferred embodiment, Hyaluronic acid and or other GAGs is used as a carrier for STRO-1$^+$ multipotential cells or progeny cells thereof. The concentration and viscosity of the hyaluronic acid/GAG composition is routinely adjusted to suit a given purpose.

In another example, the STRO-1+ multipotential cells or progeny cells thereof may be delivered in admixture with fibrin glue. When used herein the term "fibrin glue" refers to the insoluble matrix formed by the cross-linking of fibrin polymers in the presence of calcium ions. The fibrin glue may be formed from fibrinogen, or a derivative or metabolite thereof, fibrin (soluble monomers or polymers) and/or complexes thereof derived from biological tissue or fluid which forms a fibrin matrix. Alternatively, the fibrin glue may be formed from fibrinogen, or a derivative or metabolite thereof, or fibrin, produced by recombinant DNA technology.

The fibrin glue may also be formed by the interaction of fibrinogen and a catalyst of fibrin glue formation (such as thrombin and/or Factor XIII). As will be appreciated by those skilled in the art, fibrinogen is proteolytically cleaved in the presence of a catalyst (such as thrombin) and converted to a fibrin monomer. The fibrin monomers may then form polymers which may cross-link to form a fibrin glue matrix. The cross-linking of fibrin polymers may be enhanced by the presence of a catalyst such as Factor XIII. The catalyst of fibrin glue formation may be derived from blood plasma, cryoprecipitate or other plasma fractions containing fibrinogen or thrombin. Alternatively, the catalyst may be produced by recombinant DNA technology.

The rate at which the clot forms is dependent upon the concentration of thrombin mixed with fibrinogen. Being an enzyme dependent reaction, the higher the temperature (up to 37° C.) the faster the clot formation rate. The tensile strength of the clot is dependent upon the concentration of fibrinogen used.

When the fibrin clot is generated in the presence of hyaluronan it undergoes interactions and becomes interdigitated with the cross-linked matrix. This matrix is known to play a major role in tissue regeneration and performs cell regulatory functions in tissue repair [Weigel P H, Fuller G M, LeBoeuf R D. (1986) A model for the role of hyaluronic acid and fibrin in the early events during the inflammatory response and wound healing. J Theor Biol. 119: 219-34]. The dissolution rate of hyaluronan is also prolonged in the HA-Fibrin matrix which could be beneficial in prolonging the therapeutic effects of this GAG (Wadstrom J and Tengblad A (1993) Fibrin glue reduces the dissolution rate of sodium hyaluronate. Upsala J Med. Sci. 98: 159-167).

Several publications describe the use of fibrin glue for the delivery of therapeutic agents. For example, U.S. Pat. No. 4,983,393 discloses a composition for use as an intra-vaginal insert comprising agarose, agar, saline solution glycosaminoglycans, collagen, fibrin and an enzyme. Further, U.S. Pat. No. 3,089,815 discloses an injectable pharmaceutical preparation composed of fibrinogen and thrombin and U.S. Pat. No. 6,468,527 discloses a fibrin glue which facilitates the delivery of various biological and non-biological agents to specific sites within the body. However, the use of fibrin+hyaluronan+ to promote chondrogenic differentiation of STRO-1+ allogeneic cells has not been described previously.

The composition comprising STRO-1$^+$ multipotential cells and/or progeny cells thereof is "surgically added" to the disc space. That is, the material is added by the intervention of medical personnel, as distinguished from being "added" by the body's natural growth or regeneration processes. The surgical procedure preferably includes injection through a hypodermic needle, although other surgical methods of introducing the collagen-based material into the disc may be used. For example, the material may be introduced into a disc by extrusion through a dilated annular opening, infusion through a catheter, insertion through an opening created by trauma or surgical incision, or by other means of invasive or minimally invasive deposition of the materials into the disc space.

In some embodiments of the invention, it may not be necessary or desirable to immunosuppress a patient prior to initiation of therapy with cellular compositions. Indeed, the results presented herein show that transplantation of allogeneic STRO-1+ multipotential cells in sheep was well tolerated in the absence of immunosuppression.

However, in other instances it may be desirable or appropriate to pharmacologically immunosuppress a patient prior to initiating cell therapy. This may be accomplished through the use of systemic or local immunosuppressive agents, or it may be accomplished by delivering the cells in an encapsulated device. The cells may be encapsulated in a capsule that is permeable to nutrients and oxygen required by the cell and therapeutic factors the cell is yet impermeable to immune humoral factors and cells. Preferably the encapsulant is hypoallergenic, is easily and stably situated in a target tissue, and provides added protection to the implanted structure. These and other means for reducing or eliminating an immune response to the transplanted cells are known in the art. As an alternative, the cells may be genetically modified to reduce their immunogenicity.

It will be appreciated that the STRO-1+ multipotential cells or progeny thereof may be administered with other beneficial drugs or biological molecules (growth factors, trophic factors). When administered with other agents, they may be administered together in a single pharmaceutical composition, or in separate pharmaceutical compositions, simultaneously or sequentially with the other agents (either before or after administration of the other agents). Bioactive factors which may be co-administered include anti-apoptotic agents (e.g., EPO, EPO mimetibody, TPO, IGF-I and IGF-II, HGF, caspase inhibitors); anti-inflammatory agents (e.g., p38 MAPK inhibitors, TGF-beta inhibitors, statins, IL-6 and IL-1 inhibitors, PEMIROLAST, TRANILAST, REMICADE, SIROLIMUS, and NSAIDs (non-steroidal anti-inflammatory drugs; e.g., TEPOXALIN, TOLMETIN, SUPROFEN); immunosupressive/immunomodulatory agents (e.g., calcineurin inhibitors, such as cyclosporine, tacrolimus; mTOR inhibitors (e.g., SIROLIMUS, EVEROLIMUS); anti-proliferatives (e.g., azathioprine, mycophenolate mofetil); corticosteroids (e.g., prednisolone, hydrocortisone); antibodies such as monoclonal anti-IL-2Ralpha receptor antibodies (e.g., basiliximab, daclizumab), polyclonal anti-T-cell antibodies (e.g., anti-thymocyte globulin (ATG); anti-lymphocyte globulin (ALG); monoclonal anti-T cell antibody OKT3)); anti-thrombogenic agents (e.g., heparin, heparin derivatives, urokinase, PPack (dextrophenylalanine proline arginine chloromethylketone), antithrombin compounds, platelet receptor antagonists, anti-thrombin antibodies, anti-platelet receptor antibodies, aspirin, dipyridamole, protamine, hirudin, prostaglandin inhibitors, and platelet inhibitors); and anti-oxidants (e.g., probucol, vitamin A, ascorbic acid, tocopherol, coenzyme Q-10, glutathione, L-cysteine, N-acetylcysteine) as well as local anesthetics.

Genetically-Modified Cells

In one embodiment, the STRO-1+ multipotential cells and/or progeny cells thereof are genetically modified, e.g., to express and/or secrete a protein of interest, e.g., a protein providing a therapeutic and/or prophylactic benefit, e.g., insulin, glucagon, somatostatin, trypsinogen, chymotrypsinogen, elastase, carboxypeptidase, pancreatic lipase or amylase or a polypeptide associated with or causative of enhanced angiogenesis or a polypeptide associated with differentiation of a cell into a pancreatic cell or a vascular cell.

Methods for genetically modifying a cell will be apparent to the skilled artisan. For example, a nucleic acid that is to be expressed in a cell is operably-linked to a promoter for inducing expression in the cell. For example, the nucleic acid is linked to a promoter operable in a variety of cells of a subject, such as, for example, a viral promoter, e.g., a CMV promoter (e.g., a CMV-IE promoter) or a SV-40 promoter. Additional suitable promoters are known in the art and shall be taken to apply mutatis mutandis to the present embodiment of the invention.

Preferably, the nucleic acid is provided in the form of an expression construct. As used herein, the term "expression construct" refers to a nucleic acid that has the ability to confer expression on a nucleic acid (e.g. a reporter gene and/or a counter-selectable reporter gene) to which it is operably connected, in a cell. Within the context of the present invention, it is to be understood that an expression construct may comprise or be a plasmid, bacteriophage, phagemid, cosmid, virus sub-genomic or genomic fragment, or other nucleic acid capable of maintaining and/or replicating heterologous DNA in an expressible format.

Methods for the construction of a suitable expression construct for performance of the invention will be apparent to the skilled artisan and are described, for example, in Ausubel et al (In: Current Protocols in Molecular Biology. Wiley Interscience, ISBN 047 150338, 1987) or Sambrook et al (In: Molecular Cloning: Molecular Cloning: A Laboratory Manual, Cold Spring Harbor Laboratories, New York, Third Edition 2001). For example, each of the components of the expression construct is amplified from a suitable template nucleic acid using, for example, PCR and subsequently cloned into a suitable expression construct, such as for example, a plasmid or a phagemid.

Vectors suitable for such an expression construct are known in the art and/or described herein. For example, an expression vector suitable for the method of the present invention in a mammalian cell is, for example, a vector of the pcDNA vector suite supplied by Invitrogen, a vector of the pCI vector suite (Promega), a vector of the pCMV vector suite (Clontech), a pM vector (Clontech), a pSI vector (Promega), a VP 16 vector (Clontech) or a vector of the pcDNA vector suite (Invitrogen).

The skilled artisan will be aware of additional vectors and sources of such vectors, such as, for example, Invitrogen Corporation, Clontech or Promega.

Means for introducing the isolated nucleic acid molecule or a gene construct comprising same into a cell for expression are known to those skilled in the art. The technique used for a given organism depends on the known successful techniques. Means for introducing recombinant DNA into cells include microinjection, transfection mediated by DEAE-dextran, transfection mediated by liposomes such as by using lipofectamine (Gibco, Md., USA) and/or cellfectin (Gibco, Md., USA), PEG-mediated DNA uptake, electroporation and microparticle bombardment such as by using DNA-coated tungsten or gold particles (Agracetus Inc., WI, USA) amongst others.

Alternatively, an expression construct of the invention is a viral vector. Suitable viral vectors are known in the art and commercially available. Conventional viral-based systems for the delivery of a nucleic acid and integration of that nucleic acid into a host cell genome include, for example, a retroviral vector, a lentiviral vector or an adeno-associated viral vector. Alternatively, an adenoviral vector is useful for introducing a nucleic acid that remains episomal into a host cell. Viral vectors are an efficient and versatile method of gene transfer in target cells and tissues. Additionally, high transduction efficiencies have been observed in many different cell types and target tissues.

For example, a retroviral vector generally comprises cis-acting long terminal repeats (LTRs) with packaging capacity for up to 6-10 kb of foreign sequence. The minimum cis-acting LTRs are sufficient for replication and packaging of a vector, which is then used to integrate the expression construct into the target cell to provide long term expression. Widely used retroviral vectors include those based upon murine leukemia virus (MuLV), gibbon ape leukemia virus (GaLV), simian immunodeficiency virus (SrV), human immunodeficiency virus (HIV), and combinations thereof (see, e.g., Buchscher et al., *J. Virol.* 56:2731-2739 (1992); Johann et al, *J. Virol.* 65:1635-1640 (1992); Sommerfelt et al, *Virol.* 76:58-59 (1990); Wilson et al, *J. Virol.* 63:274-2318 (1989); Miller et al., *J. Virol.* 65:2220-2224 (1991); PCT/US94/05700; Miller and Rosman *BioTechniques* 7:980-990, 1989; Miller, A. D. *Human Gene Therapy* 7:5-14, 1990; Scarpa et al *Virology* 75:849-852, 1991; Burns et al. *Proc. Natl. Acad. Sci. USA* 90:8033-8037, 1993).

Various adeno-associated virus (AAV) vector systems have also been developed for nucleic acid delivery. AAV vectors can be readily constructed using techniques known in the art. See, e.g., U.S. Pat. Nos. 5,173,414 and 5,139,941; International Publication Nos, WO 92/01070 and WO 93/03769; Lehkowski et al. *Molec. Cell. Biol.* 5:3988-3996, 1988; Vincent et al. (1990) Vaccines 90 (Cold Spring Harbor Laboratory Press); Carter *Current Opinion in Biotechnology* 5:533-539, 1992; Muzyczka. *Current Topics in Microbial, and Immunol.* 158:97-129, 1992; Kotin, Human Gene Therapy 5:793-801, 1994; Shelling and Smith *Gene Therapy* 7:165-169, 1994; and Thou et al, *J Exp. Med.* 179:1867-1875, 1994.

Additional viral vectors useful for delivering an expression construct of the invention include, for example, those derived from the pox family of viruses, such as vaccinia virus and avian poxvirus or an alphavirus or a conjugate virus vector (e.g. that described in Fisher-Hoch et al., *Proc. Natl Acad. Sci. USA* 56:317-321, 1989).

EXAMPLES

Example 1

Experimental Design

Twenty four sheep received injections of 1.0 IU Chondroitinase ABC (cABC) (Seikagaku Corporation, Japan) into three adjacent lumbar discs (nominally L3-L4, L4-L5, and L5-L6) to initiate progressive disc degeneration. The remaining lumbar discs (nominally L1-L2 and L2-L3) were not injected with cABC and were considered normal controls. Fifteen weeks (±3 weeks) following administration of cABC, injections of STRO-1$^+$ multipotential cells at either a high or low dose ($4 \times 10^6$ or $0.5 \times 10^6$ cells, respectively) or ProFreeze™ NOA Freezing Medium (Lonza Walkersville Md.) mixed with an equal volume of Euflexxa® hyaluronic acid (Ferring Pharmaceuticals) were administered directly into the nucleus pulposus of the intervertebral discs (Table 1). Animals were necropsied either 3 months or 6 months post-injection. FIG. 1 is a schematic representation of the spinal levels used for the study and the protocol for the treatments.

TABLE 1

Study Design Summary

| Group | N | Disc (nominal) | 15 ± 3 weeks before Baseline | Baseline Day 0 | Tx | Analysis at Sacrifice |
|---|---|---|---|---|---|---|
| 1 | n = 6 | L1-L2 | No injection | No injection | 3 months | Histology/biochemistry |
| Low dose | | L2-L3 | No injection | No injection | 3 months | Histology/biochemistry |
| 3 Months | | L3-L4 | Chondroitinase | STRO-1$^+$ cells $0.5 \times 10^6$ | 3 months | Histology/biochemistry |
| | | L4-L5 | Chondroitinase | No injection | 3 months | Histology/biochemistry |
| | | L5-L6 | Chondroitinase | HA and NAO | 3 months | Histology/biochemistry |
| 2 | n = 6 | L1-L2 | No injection | No injection | 3 months | Histology/biochemistry |
| High dose | | L2-L3 | No injection | No injection | 3 months | Histology/biochemistry |
| 3 months | | L3-L4 | Chondroitinase | STRO-1$^+$ cells $4 \times 10^6$ | 3 months | Histology/biochemistry |
| | | L4-L5 | Chondroitinase | No injection | 3 months | Histology/biochemistry |
| | | L5-L6 | Chondroitinase | HA and NAO | 3 months | Histology/biochemistry |
| 3 | n = 6 | L1-L2 | No injection | No injection | 6 months | Histology/biochemistry |
| Low dose | | L2-L3 | No injection | No injection | 6 months | Histology/biochemistry |
| 6 months | | L3-L4 | Chondroitinase | STRO-1$^+$ cells $0.5 \times 10^6$ | 6 months | Histology/biochemistry |
| | | L4-L5 | Chondroitinase | No injection | 6 months | Histology/biochemistry |
| | | L5-L6 | Chondroitinase | HA and NAO | 6 months | Histology/biochemistry |
| 4 | n = 6 | L1-L2 | No injection | No injection | 6 months | Histology/biochemistry |
| High dose | | L2-L3 | No injection | No injection | 6 months | Histology/biochemistry |
| 6 months | | L3-L4 | Chondroitinase | STRO-1$^+$ cells $4 \times 10^6$ | 6 months | Histology/biochemistry |

TABLE 1-continued

Study Design Summary

| Group | N | Disc (nominal) | 15 ± 3 weeks before Baseline | Baseline Day 0 | Tx | Analysis at Sacrifice |
|---|---|---|---|---|---|---|
| | | L4-L5 | Chondroitinase | No injection | 6 months | Histology/biochemistry |
| | | L5-L6 | Chondroitinase | HA and NAO | 6 months | Histology/biochemistry |

Example 2

Expansion of Immunoselected STRO-1+ Multipotential Cells

The STRO-1+ multipotential cells used for these experiments were derived from French Sheep and prepared by Lonza (USA). Bone marrow (BM) aspirates were obtained from the sheep and BM mononucleiar cells (BMMNC) were prepared essentially as described previously (US 2005-0158289).

STRO-1+ multipotential cells were subsequently isolated using the STRO-3 antibody by magnetic activated cell sorting as previously described (WO2006/108229).

Example 3

Radiology

Animals had lateral plain radiographs taken of the lumbar spine under induction anaesthesia at the following time points: Day 0 (Injection of cABC), Day of Test Article administration (15±3 weeks following induction of lumbar disc degeneration) and 3 months and 6 months following implantation of the Test Article, Evaluation of the radiographs was undertaken by a blinded observer using an index of intervertebral height (DHI) calculated by averaging the measurements from the anterior, middle and posterior parts of the IVD and dividing it by the average of the adjacent intervertebral body heights as described previously (24).

Example 4

Magnetic Resonance Imagine (MRI)

MRIs were undertaken of all sheep lumbar spines under induction anaesthesia approximately 15 weeks following induction of disc degeneration by the injection of chondroitinase ABC and prior to treatment with the intradiscal injections of HA or high and low dose HA+STRO-1+ cells (Tx). Three and 6 months after treatments and immediately prior to necropsy (Nx), spinal MRI was again undertaken on all sheep.

The imaging was carried out on either of two MRI scanners. MRIs performed prior to administration of STRO-1+ cells used a 1.5 T Siemens VISION MRI scanner with Numaris 33G software. MRIs undertaken post administration of STRO-1+ cells used a 1.5 Tesla Siemens AVANTRO MRI scanner with syngo B13 software. Localizing scans were followed by sagittal imaging of the lumbar and sacral spine in T1, T1 Gradient echo (T1_Flash), T2 and STIR weightings, followed by T2 weighted axial imaging of the 6 disc levels L6/S1 L5/L6, L4/L5, L3/L4, L2/L3, L1/L2. Image sequences were provided on CDs that displayed each scan as series of 12 sagittal images. The digitised images obtained for the 12 sagittal MRI acquired sections were review by two blinded qualified observer using the Pferrmann et al classification criteria for disc degeneration scoring system (25) summarised in Table 2. The final scores corresponded to the average of the scores from the 2 blinded assessors.

TABLE 2

MRI Classification of Ovine Disc Degeneration Scoring System using the Pferrmann grading system (25)

Structure

| Homogenous, bright white | Inhomogenous with or without horizontal bands | Inhomogenous, gray | Inhomogenous, grey to black | Inhomogenous, black |
|---|---|---|---|---|
| 1 | 2 | 3 | 4 | 5 |

Distinction of Nucleus & Annulus

| Clear | Unclear | Lost |
|---|---|---|
| 1 | 2 | 3 |

Single Intensity

| Hyper-intense, iso-intense to cerebrospinal fluid | Intermediate | Hypointense |
|---|---|---|
| 1 | 2 | 3 |

Height of Intervertebral Disc

| Normal | Normal to slightly decreased | Normal to moderately decreased | Collapsed disc space |
|---|---|---|---|
| 1 | 2 | 3 | 4 |

Example 5

Histopathological Analysis

The discal units to be processed for histological and biochemical analysis were each separated by cutting through the adjacent cranial and caudal vertebral bodies close to the growth plates with a bone saw. These spinal segments were fixed en bloc in Histochoice® for 56 h and decalcified in several changes of 10% formic acid in 5% Neutral Buffered Formalin for 2 weeks with constant agitation until complete decalcification was confirmed using a Faxitron HP43855A X-ray cabinet (Hewlett Packard, McMinnville, USA).

The decalcified specimens were processed by standard histological methods for paraffin embedded and cutting. Paraffin sections 4 micron thick were mounted on Superfrost Plus glass microscope slides (Menzel-Glaser), dried at 85° C. for 30 min then at 55° C. overnight. The sections were deparaffinised in xylene (4 changes×2 min) and rehydrated through graded ethanol washes (100-70% v/v) to tap water. One section from all blocks prepared from the sagittal slices was stained with haematoxylin and eosin (H&E). The H&E stained histological sections were coded and reviewed to assess the extent of degeneration by an independent blinded histopathologist using a published (26) four-point semi-quantitative grading system (see Table 3). Additional tinctorial stains including Alcian Blue counter-stained with Neutral Red were also used to identify the distribution and assembly of matrix components in the disc sections.

considered significant. For the histological and MRI aggregate degeneration and NP scores, comparison between the various disc treatments was undertaken using the Kruskal-Wallis or Friedman Tests (nonparametric repeated measures ANOVA) with Dunn's multiple comparison post hoc test. Statistical significance between groups was taken as $p<0.05$.

TABLE 3

Grading system of histologic changes in lower lumbar discs (BEP bony end-plate, CEP cartilaginous end-plate)

| Grade | Annulus fibrosis | Nucleus pulposus | Cartilage end-plate | Margins/subchondral bone |
|---|---|---|---|---|
| 1 | Intact lamellae<br>Narrow inter-lamellar matrix<br>Intact annulus attachment<br>Vessels only in outer ⅓ | Homogeneity<br>Absence of clefting | Uniform thickness<br>Intact attachment to bone<br>Uniform calcification <⅓ of depth<br>Uniform cell distribution | Even thickness of BEP<br>Lamellar bone only<br>Distinct junction with CEP<br>Few vascular intrusions into CEP |
| 2 | Minor lamellar splitting and disorganisation. Minor widening of matrix Minor disorganisation of attachment Rim lesion without reparative reaction | Minor clefting<br>Minor cell necrosis<br>Minor posterior displacement of annulus<br>Minor chondrone formation | Minor cartilage thinning<br>Small transverse fissures<br>Irregular thickening of calcified zone<br>Few invading vascular channels<br>Small chondrones | Slightly uneven BEP<br>Schmorl's nodes<br>Minimal remodelling of BEP<br>Small marginal osteophytes |
| 3 | Moderate widening of matrix moderate fissuring of attachment Radiating tears not involving outer ⅓ minimal chondroid metaplasia Cystic degeneration Vessels in outewr and middle ⅓ rim lesion with minor reparative reaction | Moderate clefting<br>Moderate cell necrosis<br>Cystic degeneration<br>Posterior displacement within annulus<br>Centripetal extension of collagen<br>Moderate chondrone formation | Marked cartilage thinning<br>Marked thickening of calcified zone<br>Many transverse fissures<br>Many vascular channels<br>Many chondrones | Moderately uneven BEP<br>Vascularised Schmorl's nodes<br>Moderate trabecular thickening<br>Defect in bone lamellae<br>Minimal fibrosis tissue in marrow spaces<br>Medium-size osteophytes |
| 4 | Extensive lamellar disorganisation<br>Radiating tears extending into outer ⅓<br>Extensive chondroid metaplasia<br>Vessels in all zones<br>Rim lesion with marked reparative reaction | Complete loss of nucleus<br>Loose body formation<br>Marked chondrone formation | Total loss of cartilage<br>Calcification of residual cartilage<br>Widespread fissuring | Marked uneven BEP<br>Ossified Schmorl's nodes<br>Large osteophytes<br>Marked trabecular thickening<br>Marked fibrosis of marrow spaces<br>Cartilage formation |

Example 6

Biochemical Analysis of Fixed Disc Tissue

The annulus fibrosus (AF) and nucleus pulposus (NP) were carefully dissected from the processed decalcified disc tissues remaining after the central sagital slice was removed for the histological studies. This process was more difficult for grossly degenerate discs where the demarcation boundary between the NP and AF was lost. Aliquots of the finely diced NP and AF tissues were freeze dried to constant weight and triplicate portions (1-2 mg) of the dried tissues were hydrolysed in 6M HCl at 110° C. for 16 h. Aliquots of the neutralised digests assayed for hydroxyproline as a measure of the tissue collagen content as described previously (4). Triplicate portions of freeze dried tissues (~2 mg) were also digested with papain and aliquots assayed for sulphated glycosaminoglycan (GAGs) using the metachromatic dye 1,9-dimethylmethylene blue as described previously (27).

Example 7

Statistical Analysis of Data

The statistical comparison of the DHIs and the biochemical data for all the 3 and 6 month treatment groups was undertaken using the Student's unpaired t-test where $p<0.05$ was Example 8

Results of the Ovine Disc Re-Generation Studies Using Immunoselected STRO-1$^+$ Multipotential Cells All animals in the high dose ($4.0 \times 10^6$ STRO-1$^+$ cells) (Groups 2 and 4) and low dose ($0.5 \times 10^6$ STRO-1$^+$ cells) (Groups 1 and 3) injected groups maintained normal body weights and showed no evidence of adverse side effects over the duration of the experiment.

Figure 2:
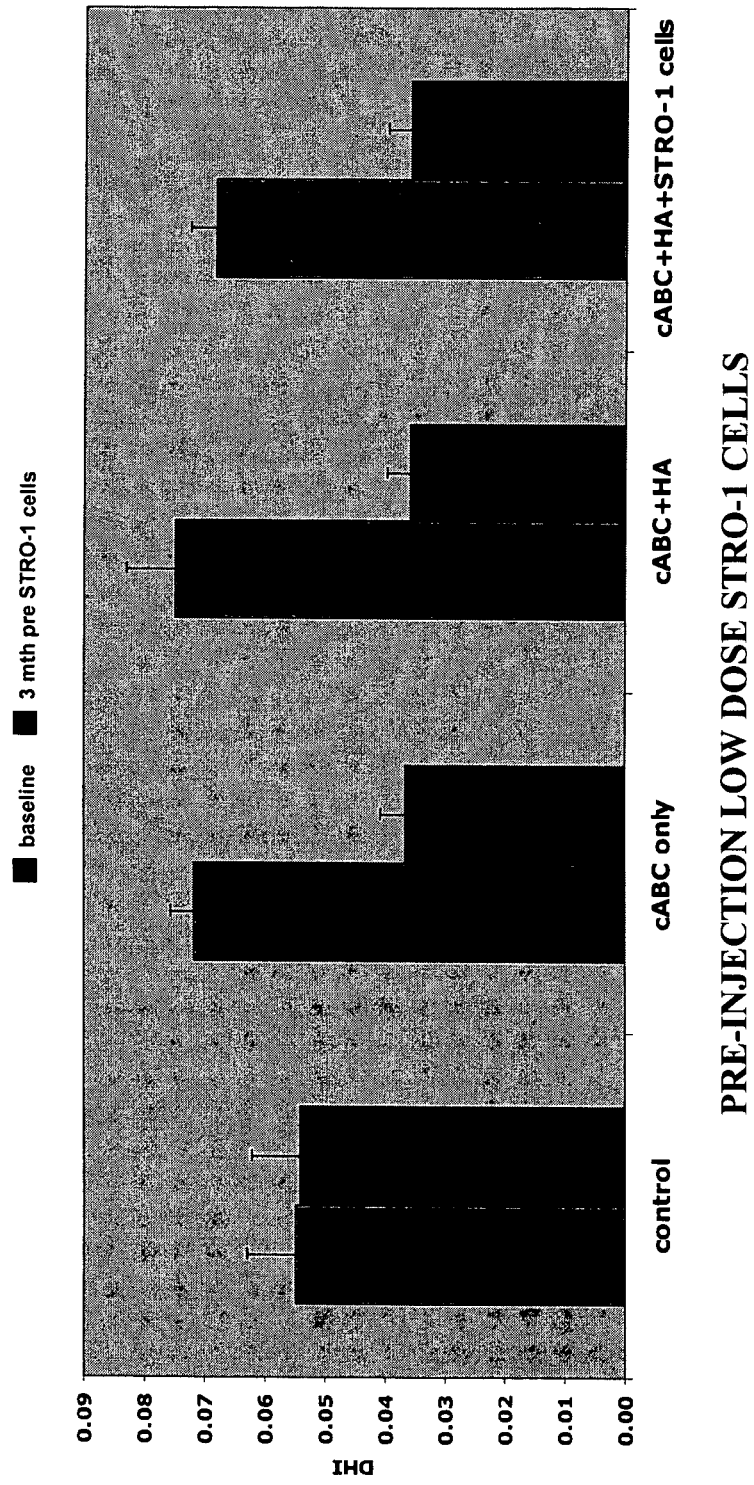
FIG. 2. Radiologically determined Disc Height Index (DHI). X-Ray determined mean±SEM Disc Height Index (DM) at baseline and 3 months after Chondroitinase ABC induced degeneration (3 mth pre-STRO-1 cells) for the sheep group who received low dose (A) and high dose (B) STRO-1 cells.
Figure 2:
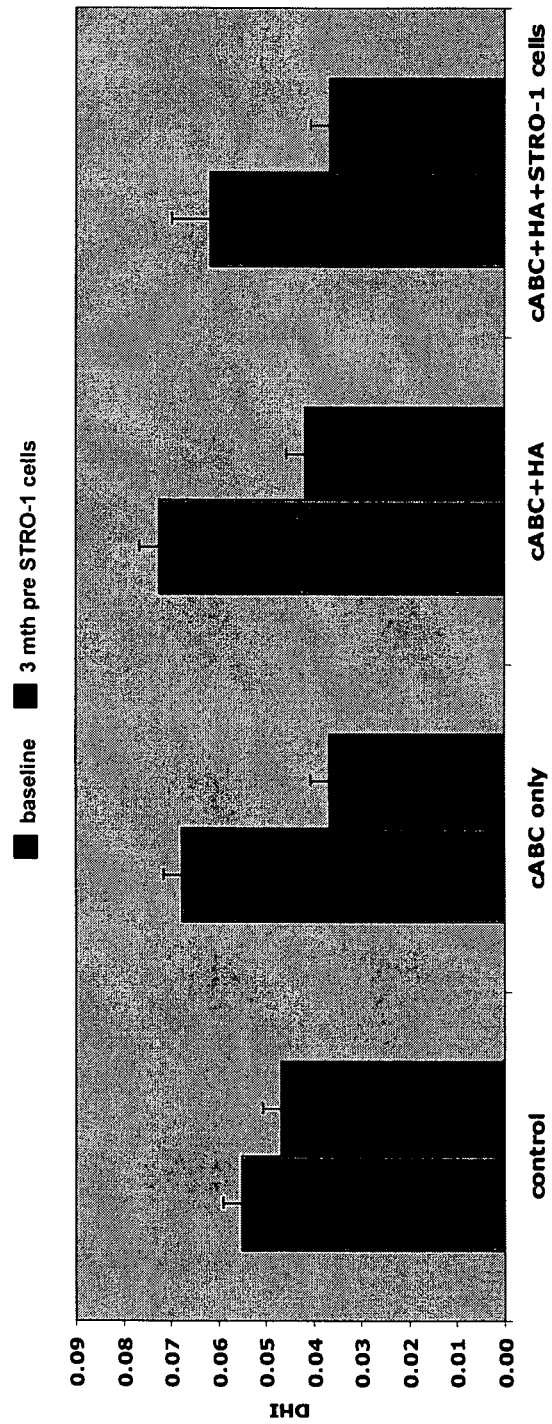
Figure 3:
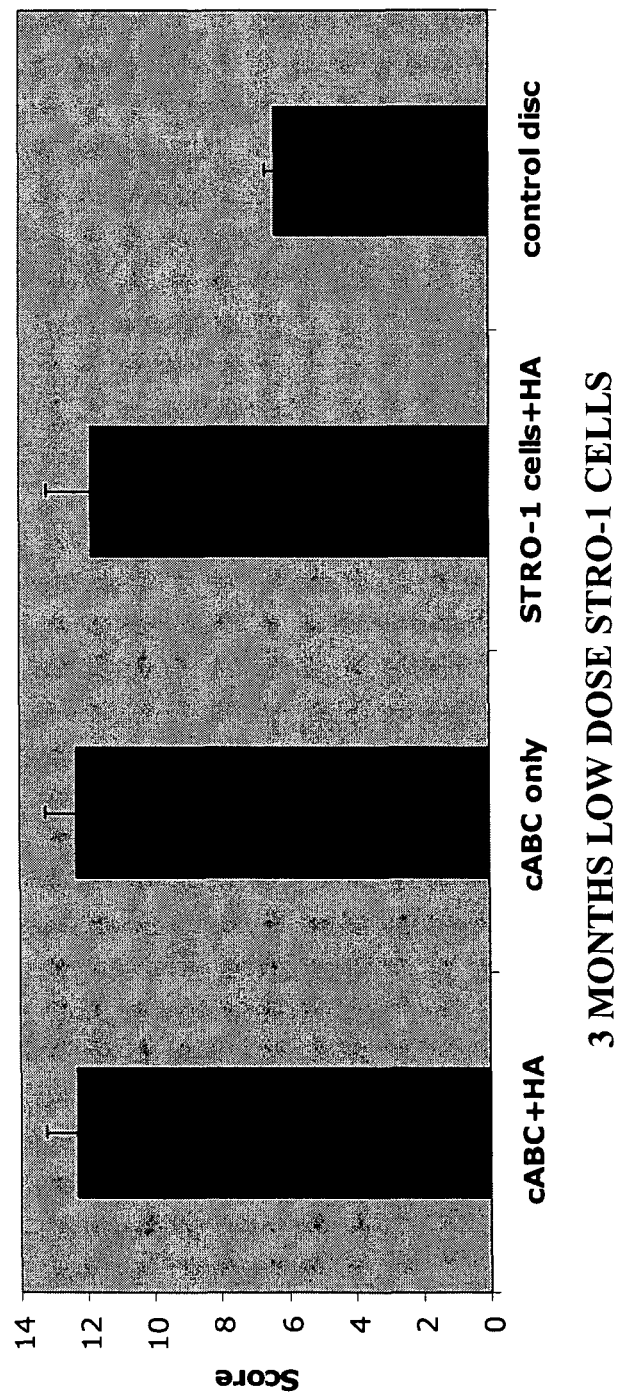
FIG. 3: MRI determined aggregate disc degeneration scores for chondroitinase ABC injected discs. Mean±SEM of MRI determined aggregate disc degeneration scores after injection with chondroitinase ABC prior to treatment with low dose STRO-1 cells+HA or HA alone for 3 months (A) or 6 months (B).
Figure 3:
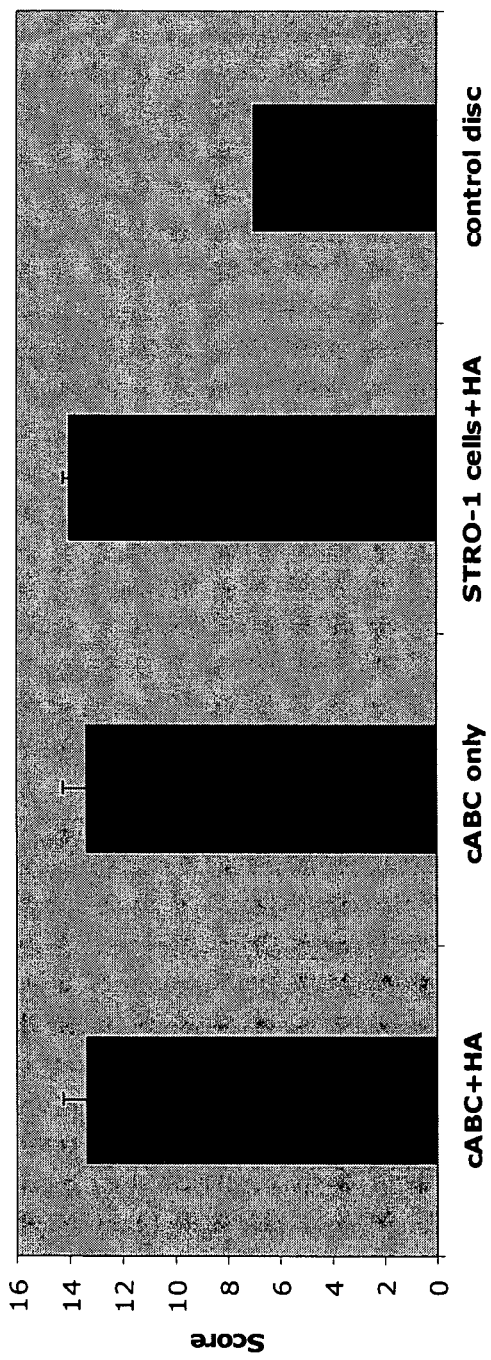
Figure 4:
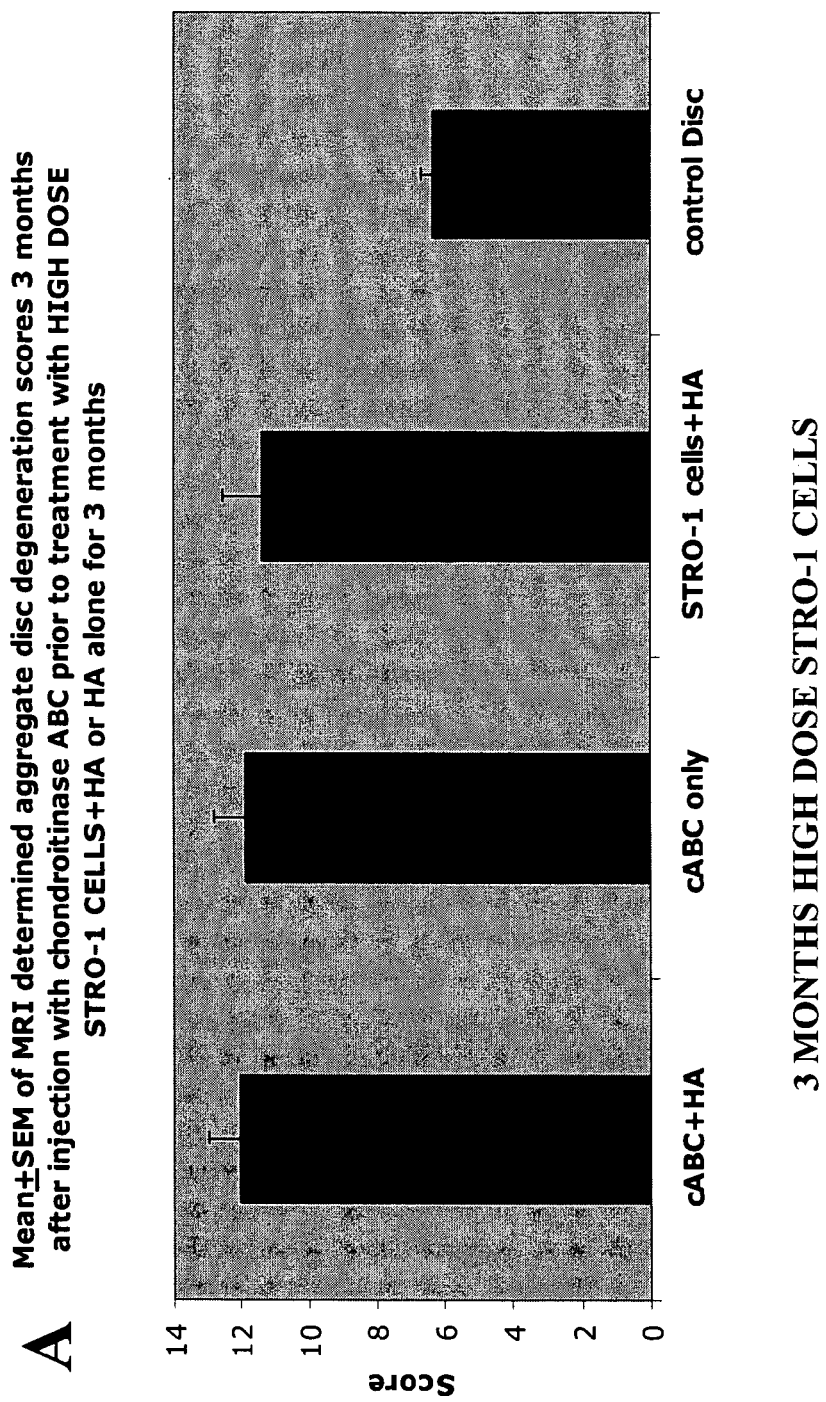
FIG. 4: MRI determined aggregate disc degeneration scores for chondroitinase ABC injected discs. Mean±SEM of MRI determined aggregate disc degeneration scores after injection with chondroitinase ABC prior to treatment with low dose STRO-1 cells+HA or HA alone for 3 months (A) or 6 months (B).
Figure 4:
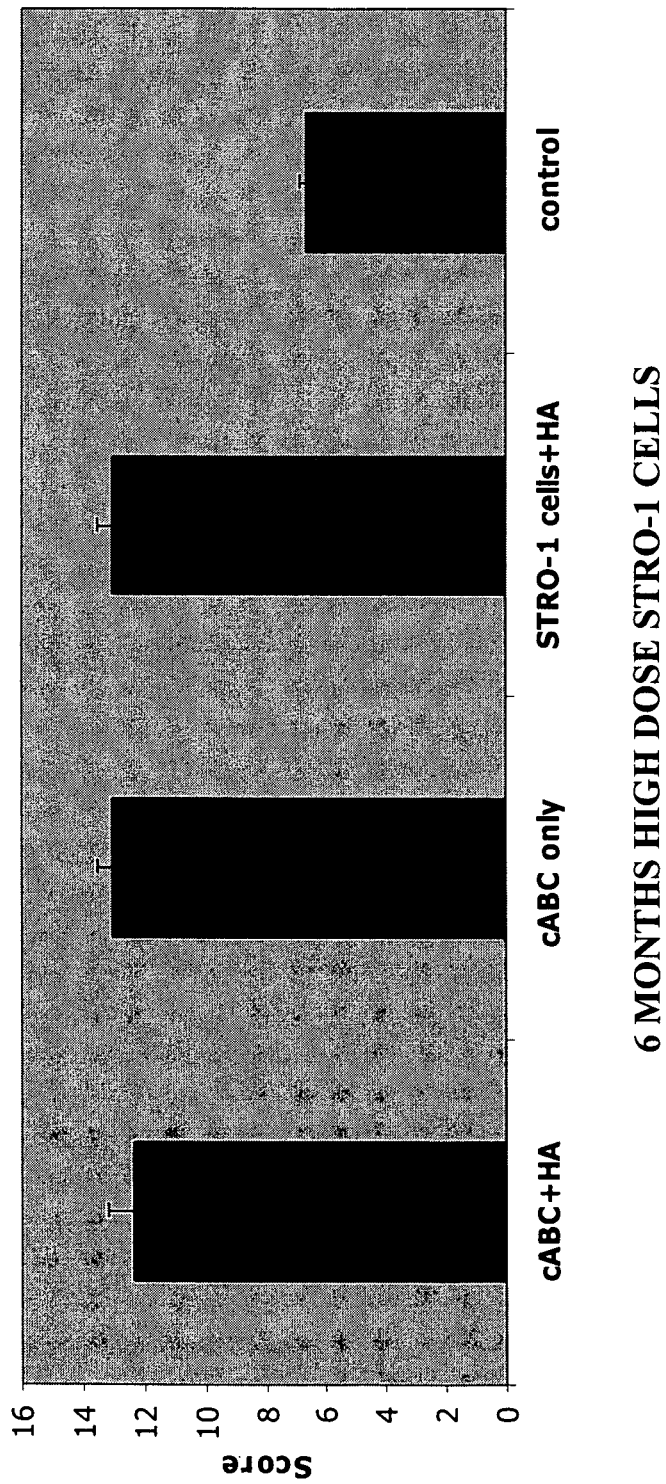

The injection of the chemonucleolytic agent, chondroitinase ABC, into the NP of target discs resulted in an approximate 50% decrease in disc height index (DHI) over 3 months as shown in FIG. 2; confirming a significant loss of PGs and water from the disc extra-cellular matrix. The DHI pre-treatment data was supported by the MRI aggregate disc degeneration scores. As shown in FIGS. 3 and 4, for all groups, the non-chondroitinase ABC injected control discs afforded MRI degeneration scores that were approximately 50% of the chondroitinase ABC injected disc scores confirming the validity of the model.

Figure 5:
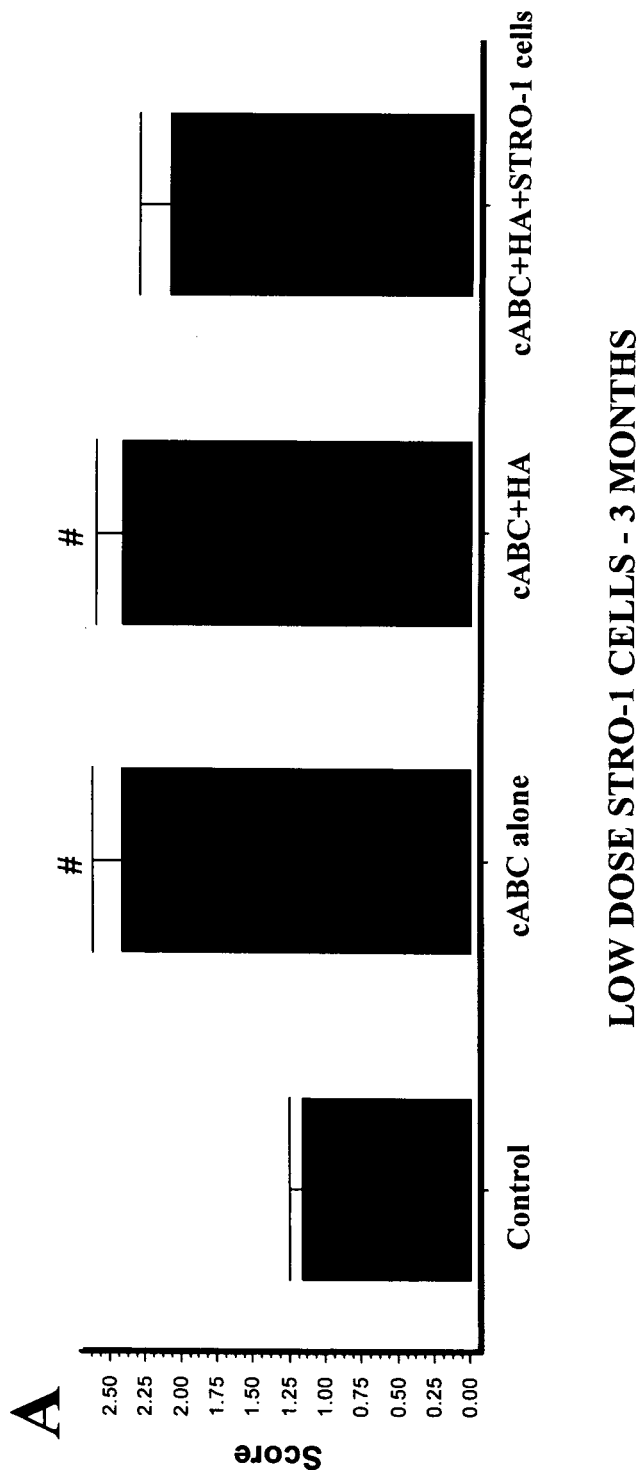
FIG. 5: Aggregate Histopathology Disc Degeneration Scores. Means of aggregate histopathology disc degeneration scores at 3 months (A) and 6 months (B) for low dose STRO-1 cells. #=significantly different from control $p<0.001$. Ω=from STRO-1$^+$ cells $p<0.01$
Figure 5:
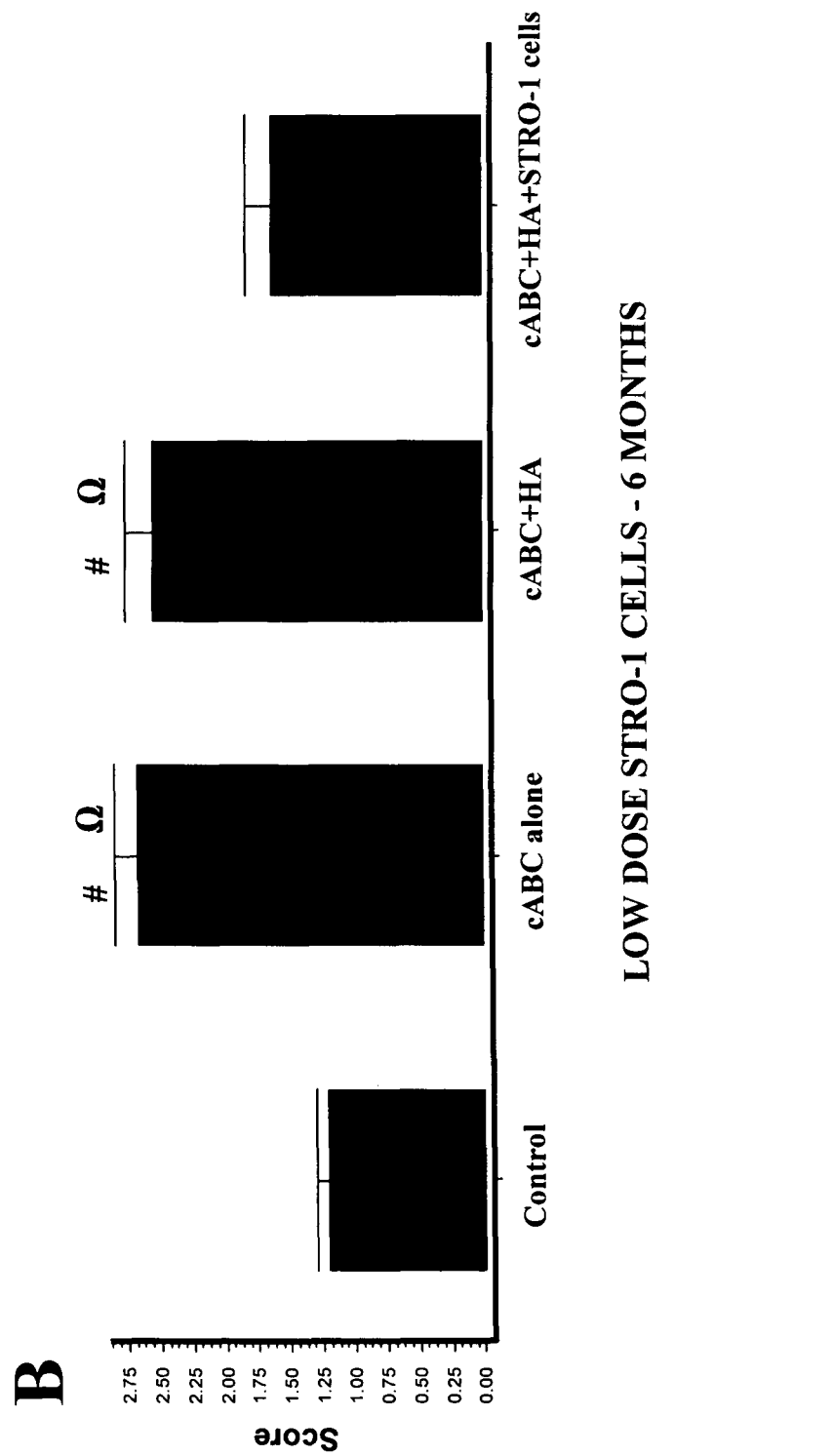
Figure 6:
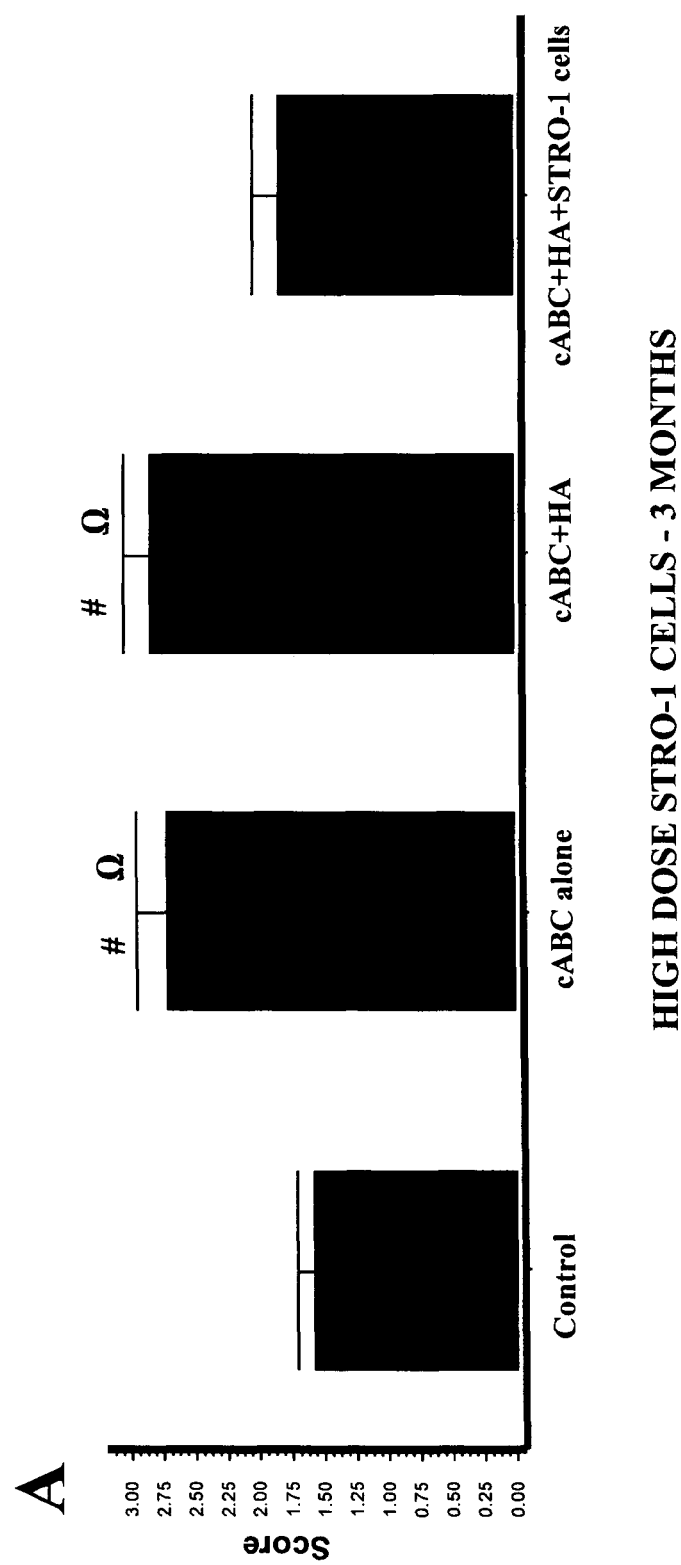
FIG. 6: Aggregate Histopathology Disc Degeneration Scores. Means of aggregate histopathology disc degeneration scores at 3 months (A) and 6 months (B) for high dose STRO-1 cells. #=significantly different from control $p<0.001$. Ω=from STRO-1$^+$ cells $p<0.01$
Figure 6:
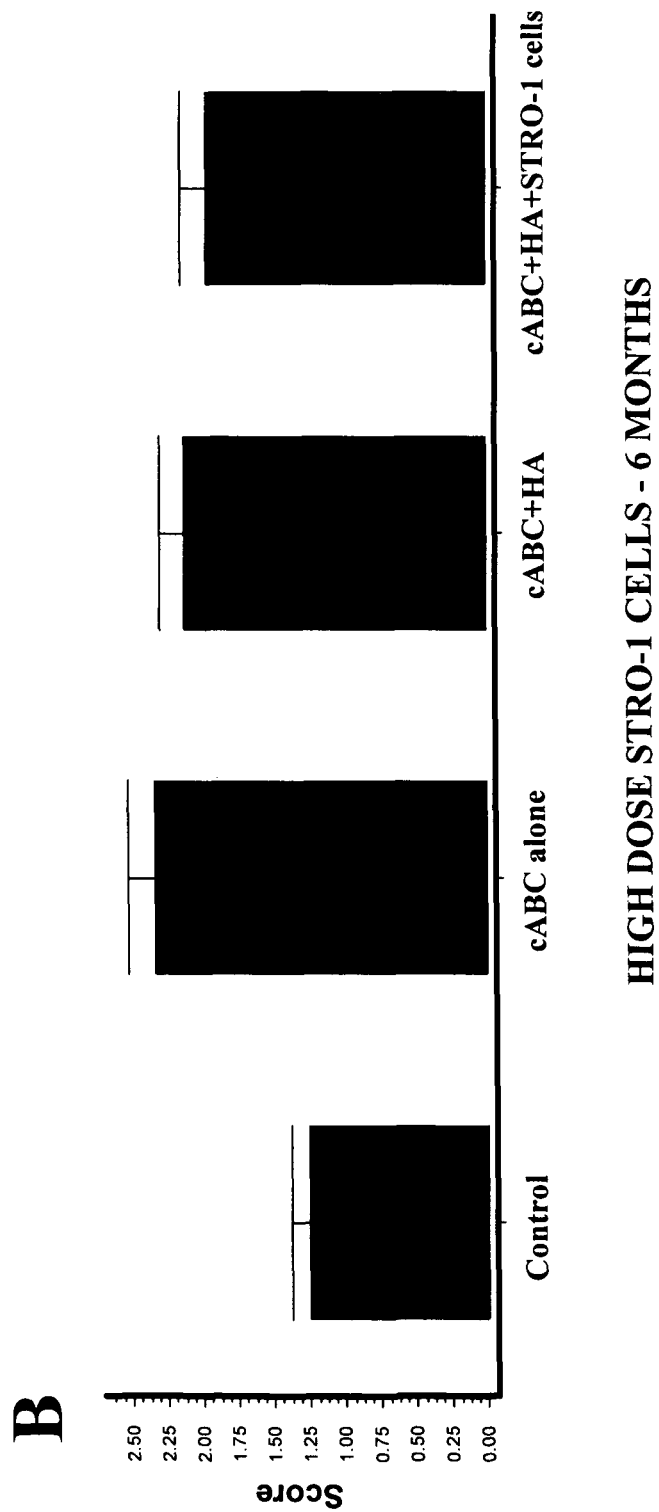

The aggregate of the mean histopathological grading scores determined for the discs of animals sacrificed 3 months after injection with low dose STRO-1$^+$ cells showed a decline in scores which were not significantly different to the non-injected control disc nor the cABC or cABC+HA injected discs. However, the latter 2 scores were significantly higher ($p<0.001$) than control disc scores (FIG. 5A). For the low dose STRO-1$^+$ cells group that was sacrificed 6 months post treatments the disc scores were significantly lower ($p<0.01$) than the cABC and cABC+HA injected discs but were equivalent to the non-injected control disc scores (FIG. 5B). This pattern was maintained for the high dose STRO-1+ cells discs at 3 months (p<0.05) (FIG. 6A) but not 6 months post injection (FIG. 6B).

Photomicrographs of histological sections of non-injected control, cABC, cABC+HA and cABC+STRO-1+ cells injected discs of a 3 months low dose sheep and 6 months low dose sheep together with their respective histopathological scores were analysed. This analysis highlighted the marked structural and cellular variations resulting from the various intra-discal treatments post cABC administration. It also illustrated the beneficial effects mediated by the STRO-1+ cells as demonstrated by the normalization of disc structural integrity and deposition of a new extracellular matrix 6 months following administration of the low dose of cells. Although these histological sections were selected on the basis of their diverse histopathological scores, they were consistent with the overall mean aggregate scores obtained for all the 3 and 6 months low dose groups summarized in FIG. 5.

Figure 7:
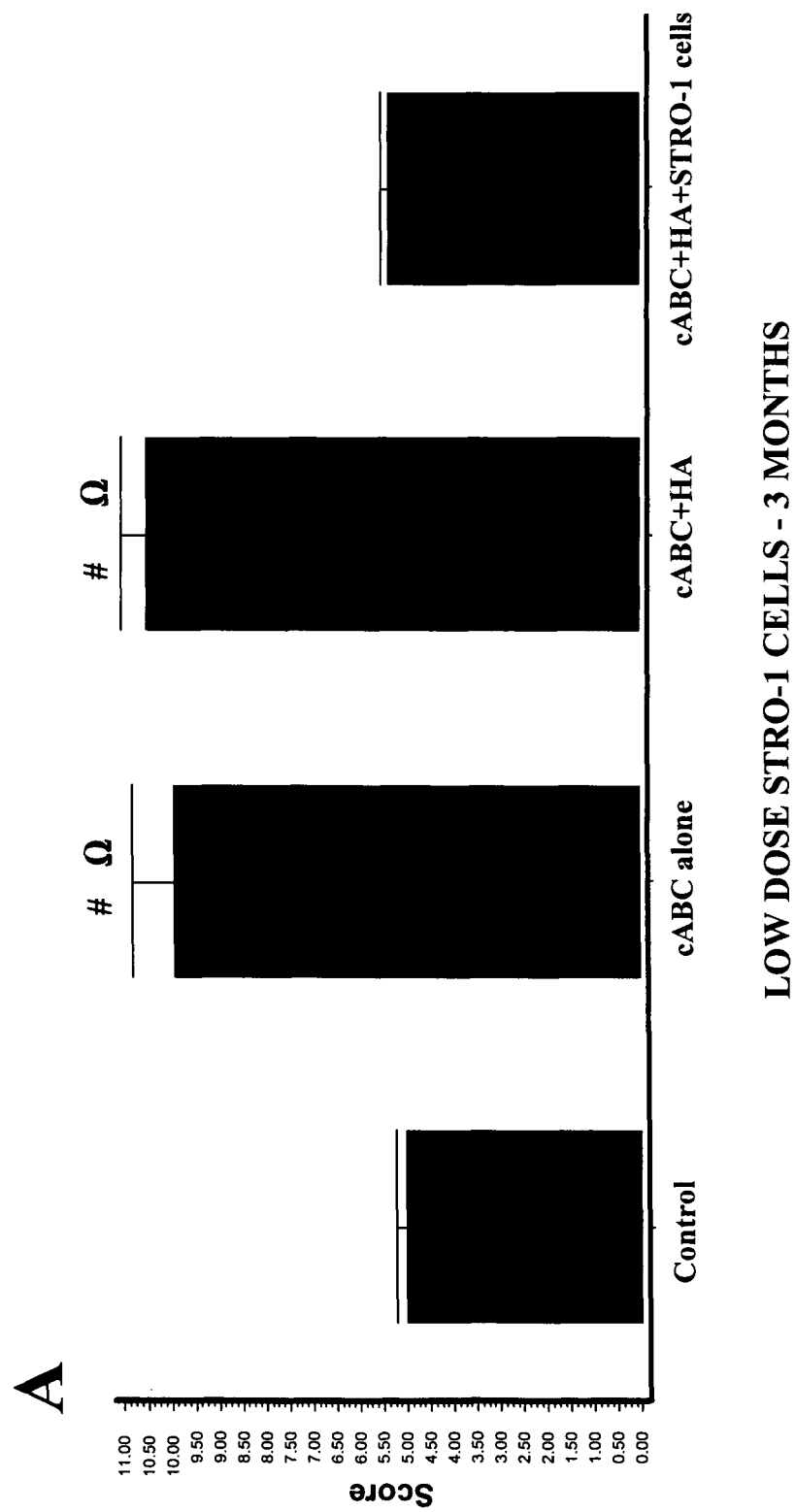
FIG. 7: Aggregate MRI Disc Degeneration Scores. Aggregate MRI disc degeneration scores for low dose STRO-1 cells at 3 months (A) and 6 months (B). #=significantly different from control $p<0.05$. Ω=from STRO-1$^+$ cells $p<0.05$
Figure 7:
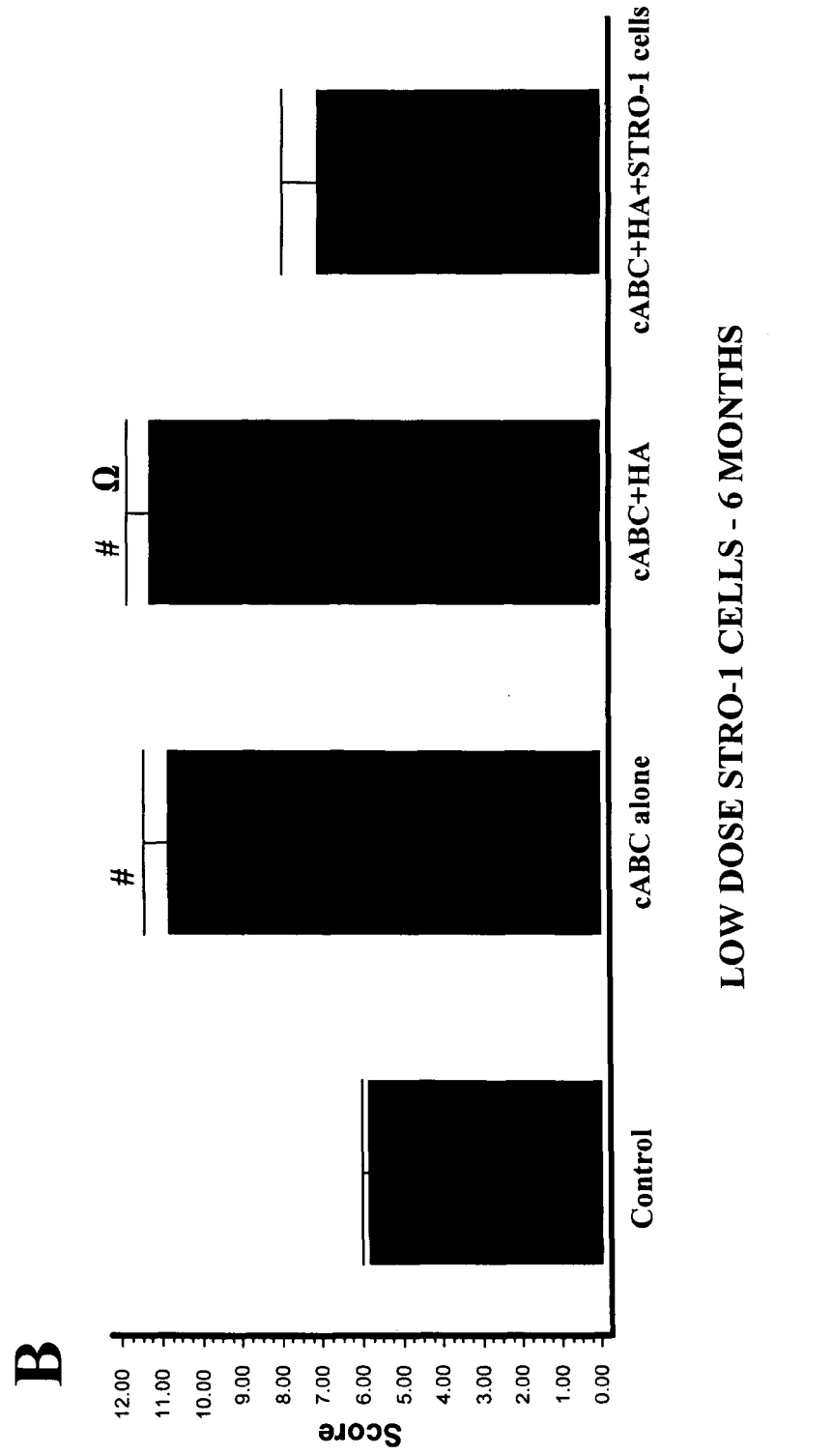
Figure 8:
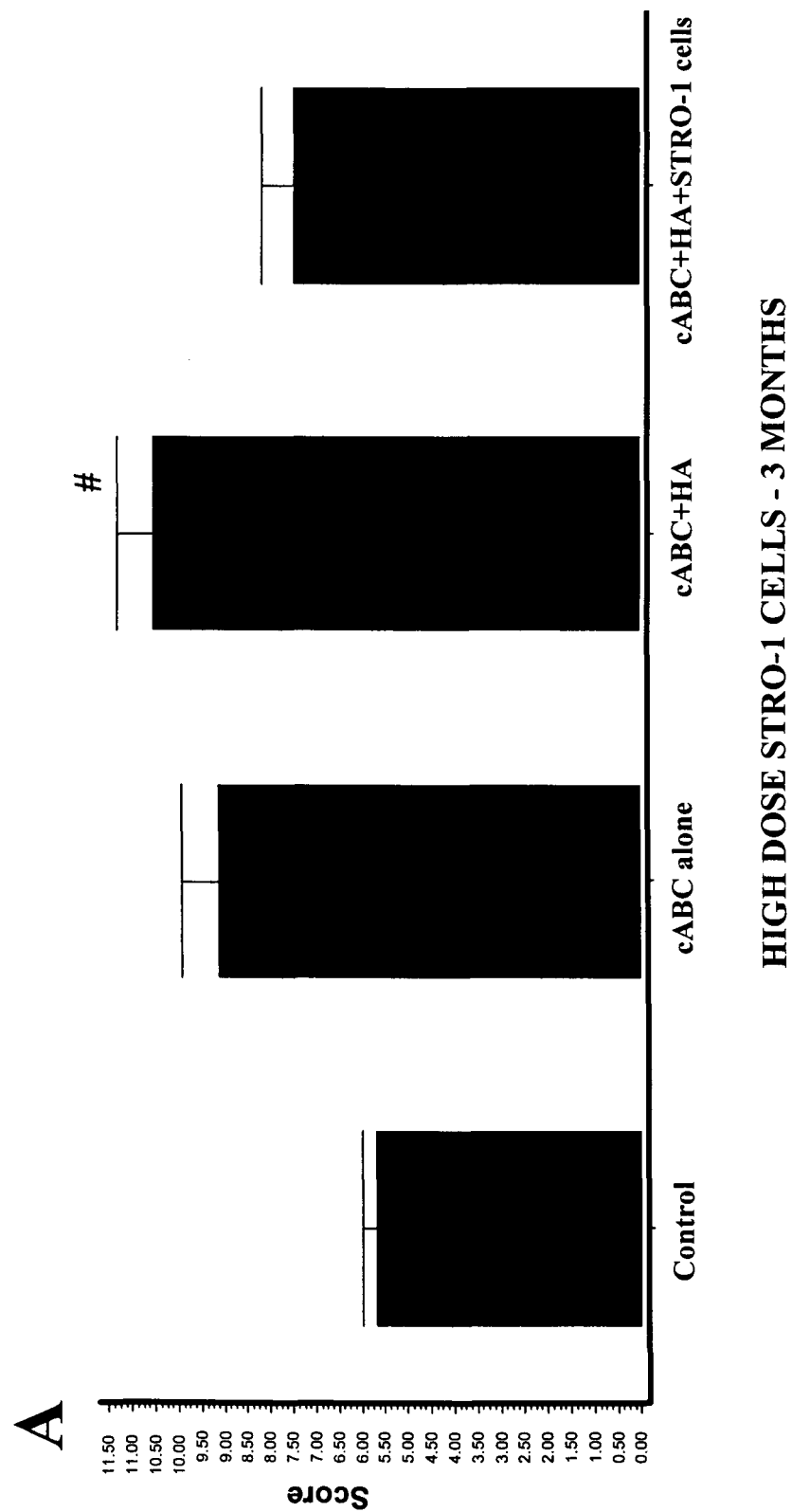
FIG. 8: Aggregate MRI Disc Degeneration Scores. Aggregate MRI disc degeneration scores for high dose STRO-1 cells at 3 months (A) and 6 months (B). #=significantly different from control $p<0.05$. Ω=from STRO-1$^+$ cells $p<0.05$
Figure 8:
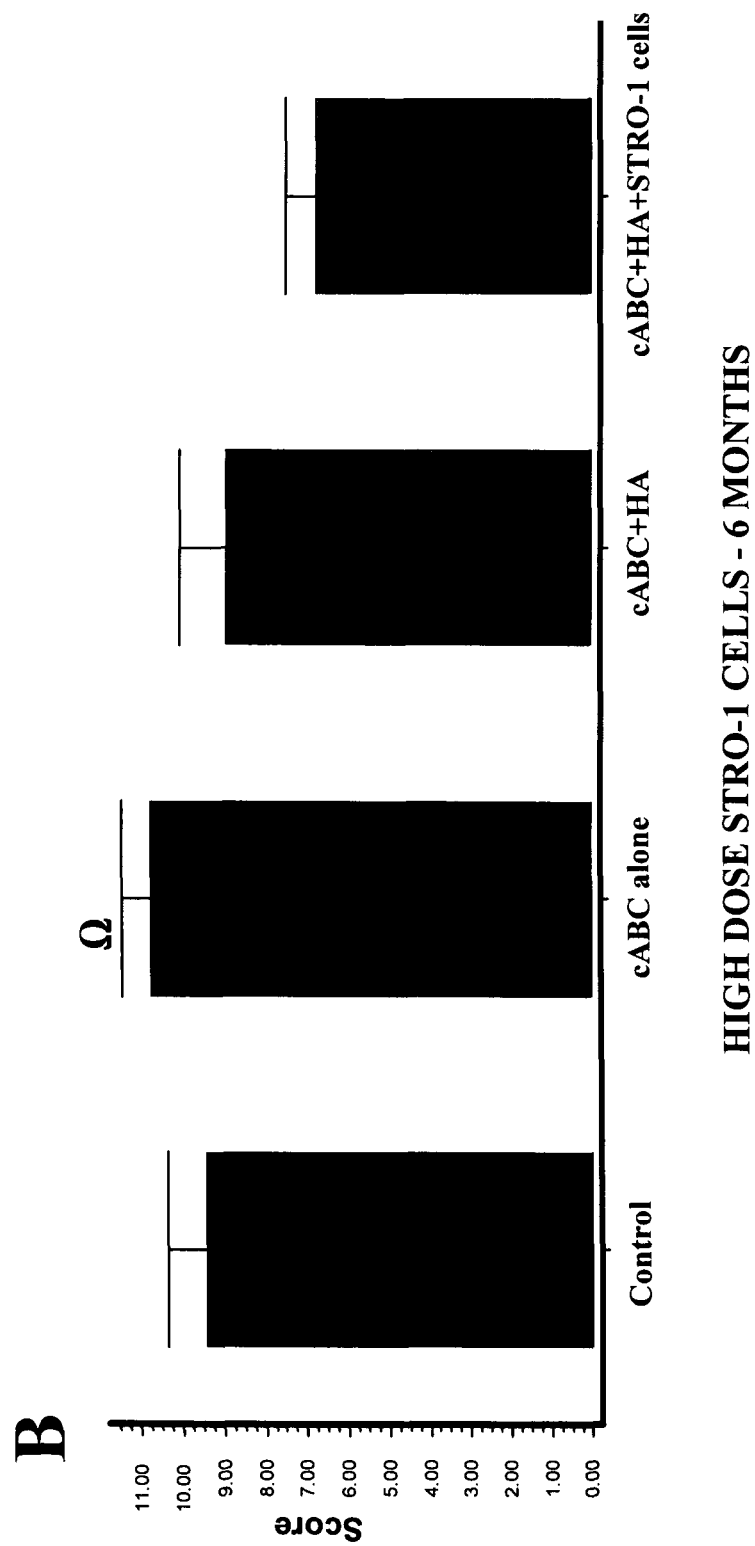

The disc histopathology scores were complimentary with the MRI assessed disc degeneration scores. Moreover, in all groups the MRI scores followed the same pattern of higher scores for the cABC alone and cABC+HA injected discs than for the cABC+STRO-1+ cells and control discs scores irrespective of the dose used. However, for the MRI degeneration scores, significant differences were observed for both the 3 and 6 months low dose STRO-1+ cells injected disc scores relative to the cABC+HA scores (p<0.05) (FIGS. 7A & 7B). MRI scores for high dose injected STRO-1+ cells were not significantly different from control, cABC alone or cABC+HA values at 3 months but were less than cABC alone at 6 months (FIGS. 8A and 8B).

Figure 9:
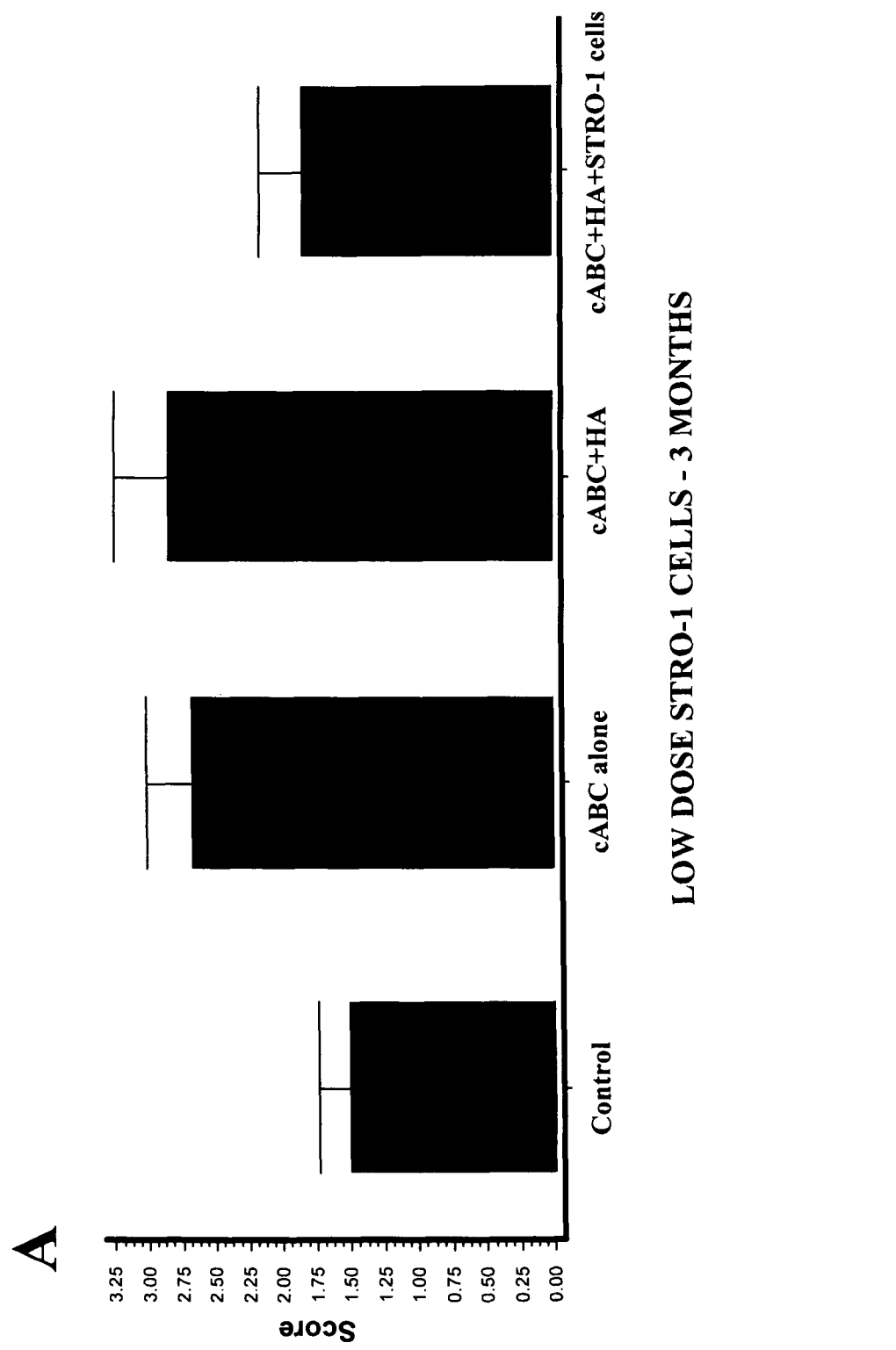
FIG. 9: Nucleus Pulposus (NP) Histopathology Degeneration Scores. Means of NP histopathology degeneration scores for low dose STRO-1 cells at 3 months (A) and 6 months (B).
Figure 9:
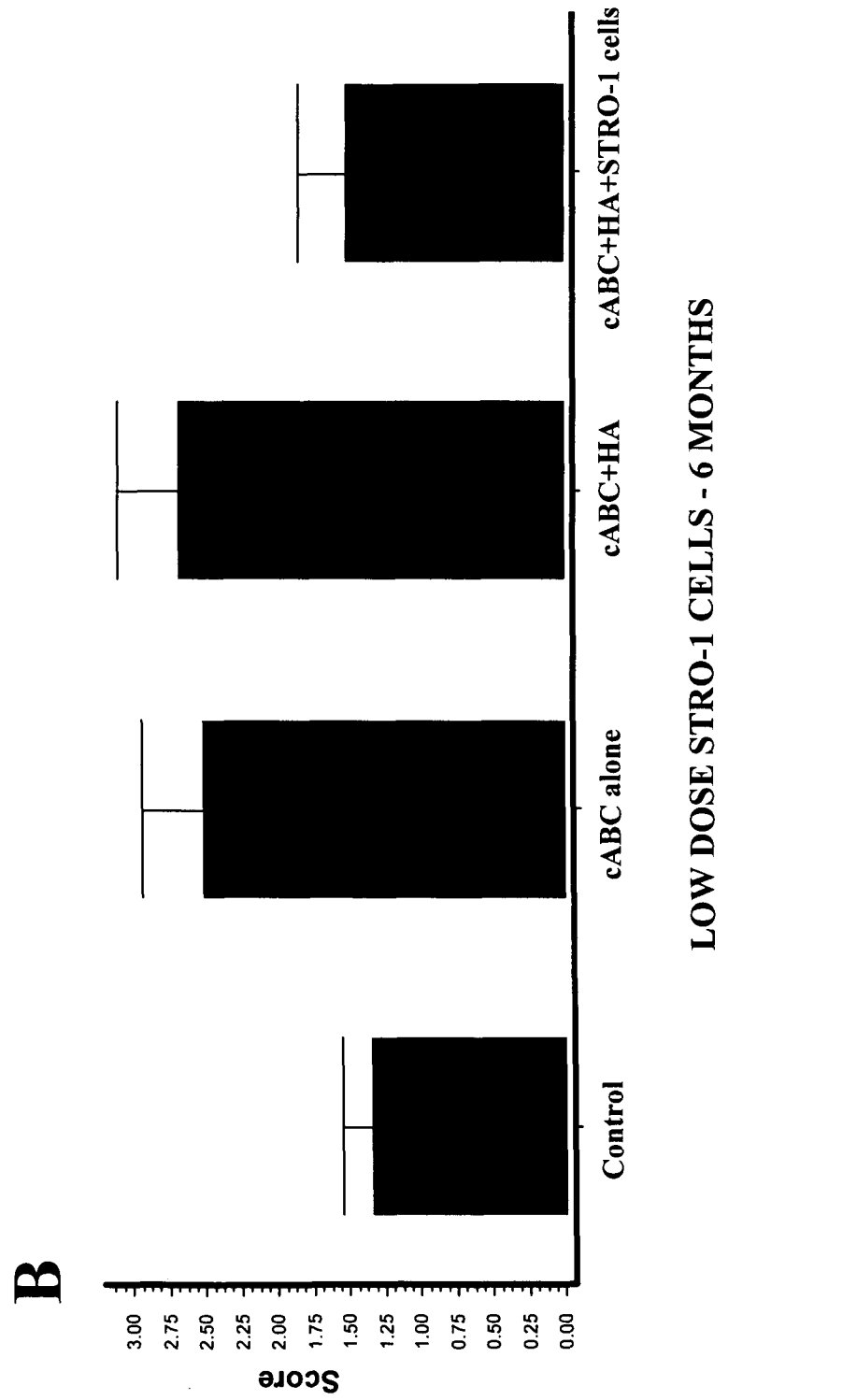
Figure 10:
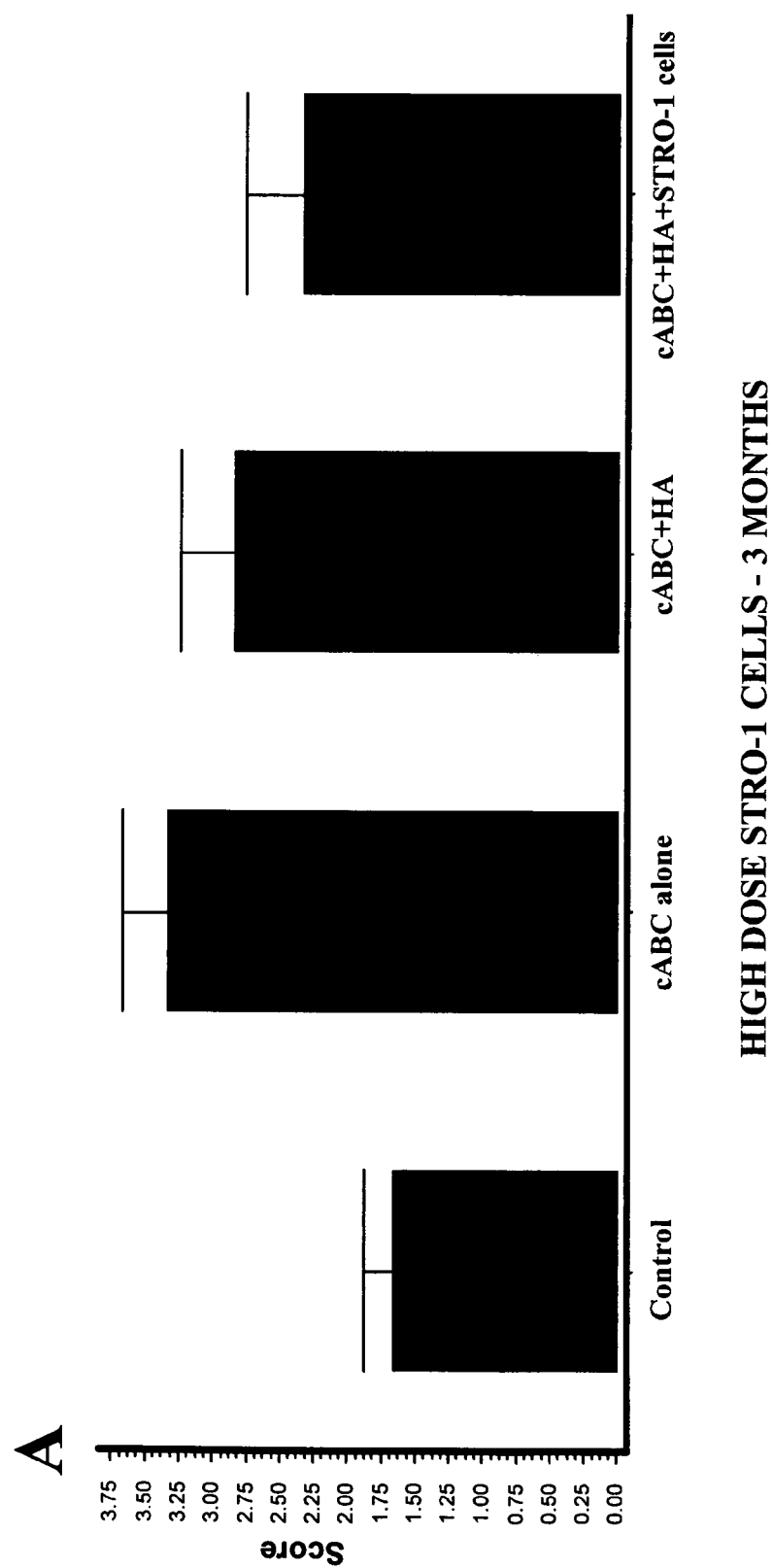
FIG. 10: Nucleus Pulposus (NP) Histopathology Degeneration Scores. Means of NP histopathology degeneration scores for high dose STRO-1 cells at 3 months (A) and 6 months (B).
Figure 10:
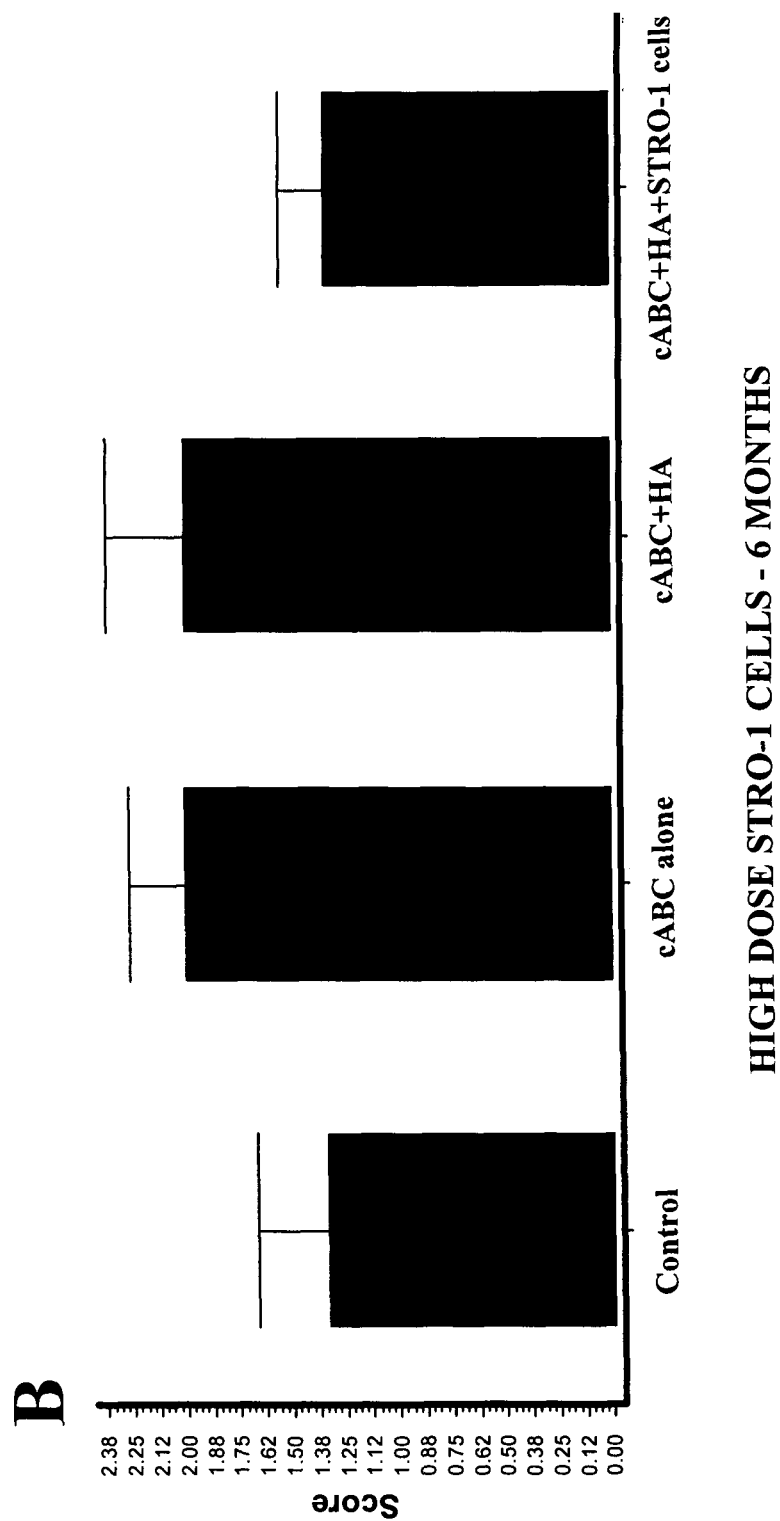

Since the experimental model of disc degeneration used in these experiments was induced by the injection of the PG depolymerising enzyme, chondroitinase-ABC, directly into the NP, the histolopathology scores for this region are shown separately. In addition the biochemical changes that occurred in response to the various treatments for the NP tissues are also presented. As is evident from FIGS. 9 and 10 the mean NP histopathology scores for the cABC+STRO-1+ cells injected discs followed the same pattern as the overall disc histopathology scores with the cABC and cABC+HA injected discs exhibiting higher degeneration scores. However, differences were not statistically significant due to inter-animal sample variation within the small group sizes used (N=6).

The radiologically determined disc height index (DHI) is a validated index of disc degeneration (24). As already discussed DHI were reduced by about 50% three months following intra-discal injection of the PG depolymerising enzyme, cABC.

Figure 11:
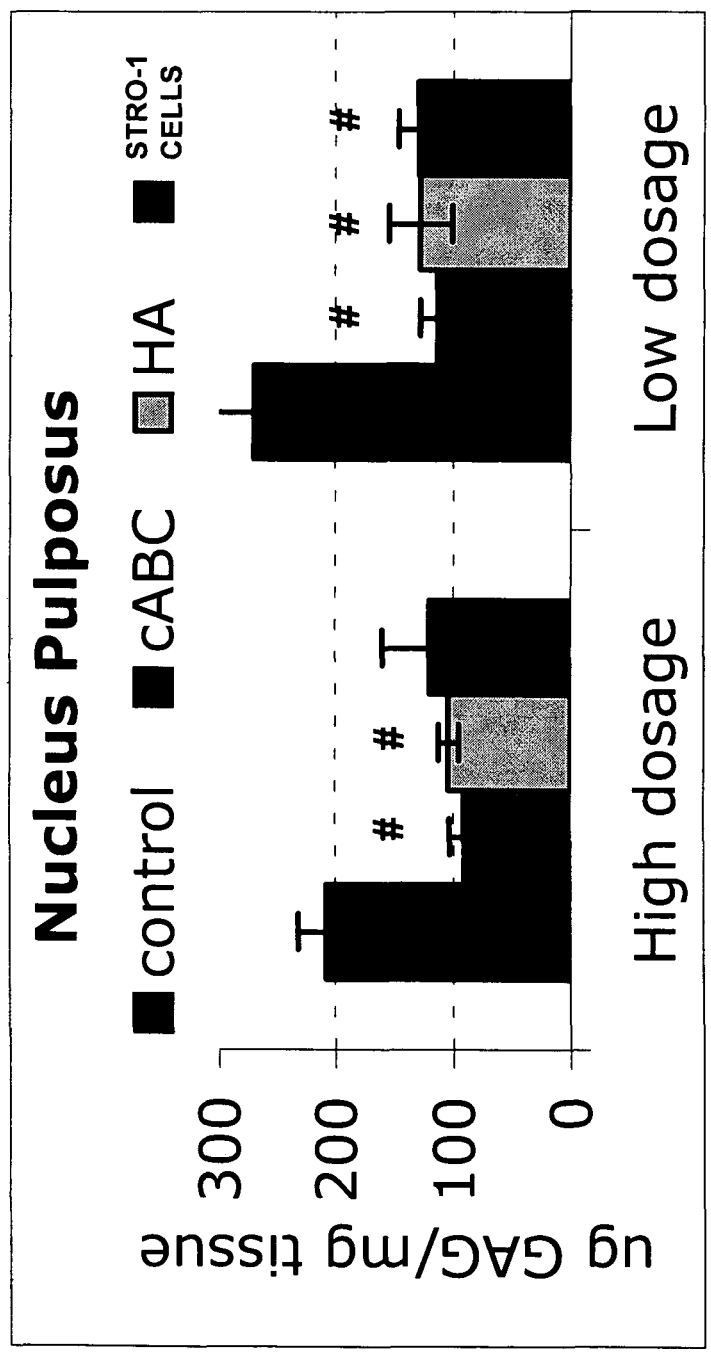
FIG. 11. Biochemically determined glycosaminoglycan (GAG) content for Nucleus Pulposus. Mean±SD Biochemically determined glycosaminoglycan (GAG) content for the Nucleus Pulposus for Discs injected with Low dose or High dose STRO-1 cells for 3 months (A) or 6 months (B). #=significantly different from control ($p<0.05$).
Figure 11:
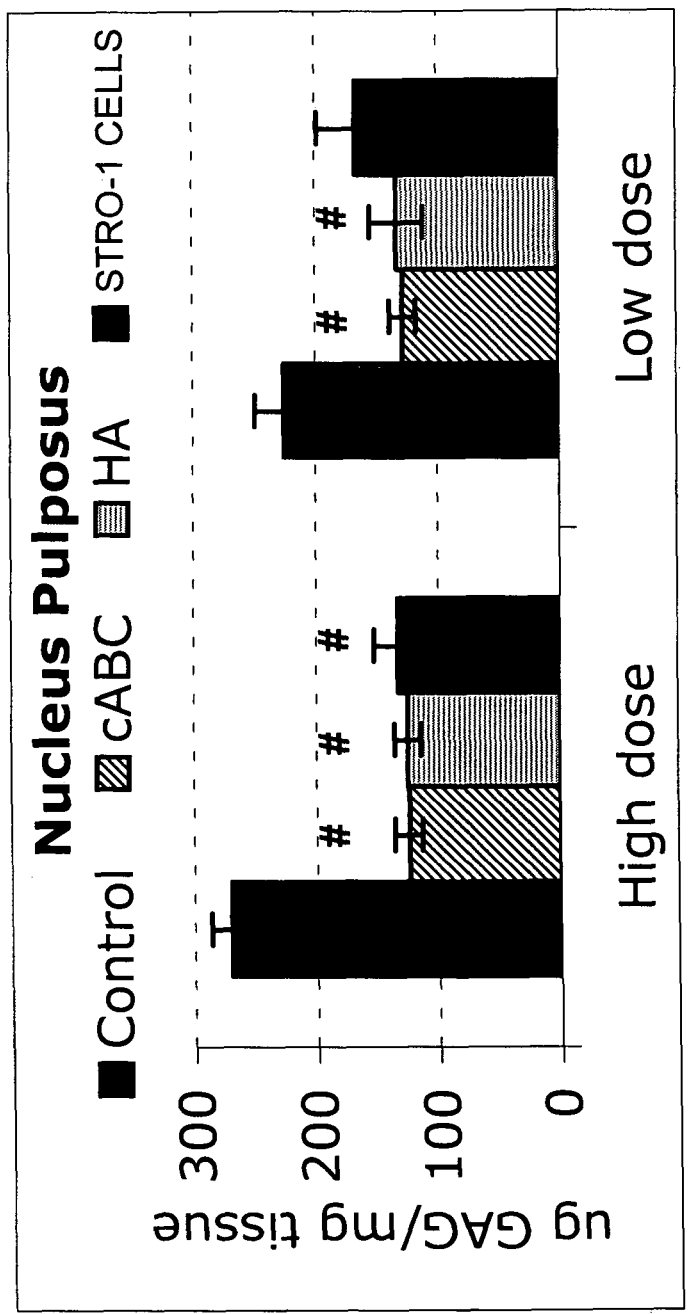

Biochemical determination of the glycosaminoglycan (GAG) content (as a marker of PGs) of the disc NP tissues showed a substantial loss in this component for all treated discs relative to the non-injected control discs (FIG. 11). While significant differences (p<0.05) in GAG levels were observed for the cABC and cABC+HA tissues relative to control NP tissues for all groups, high dose STRO-1+ cells injected discs at 3 months and low dose STRO-1+ cells at 6 months were not statistically different to controls (FIG. 11).

Figure 12:
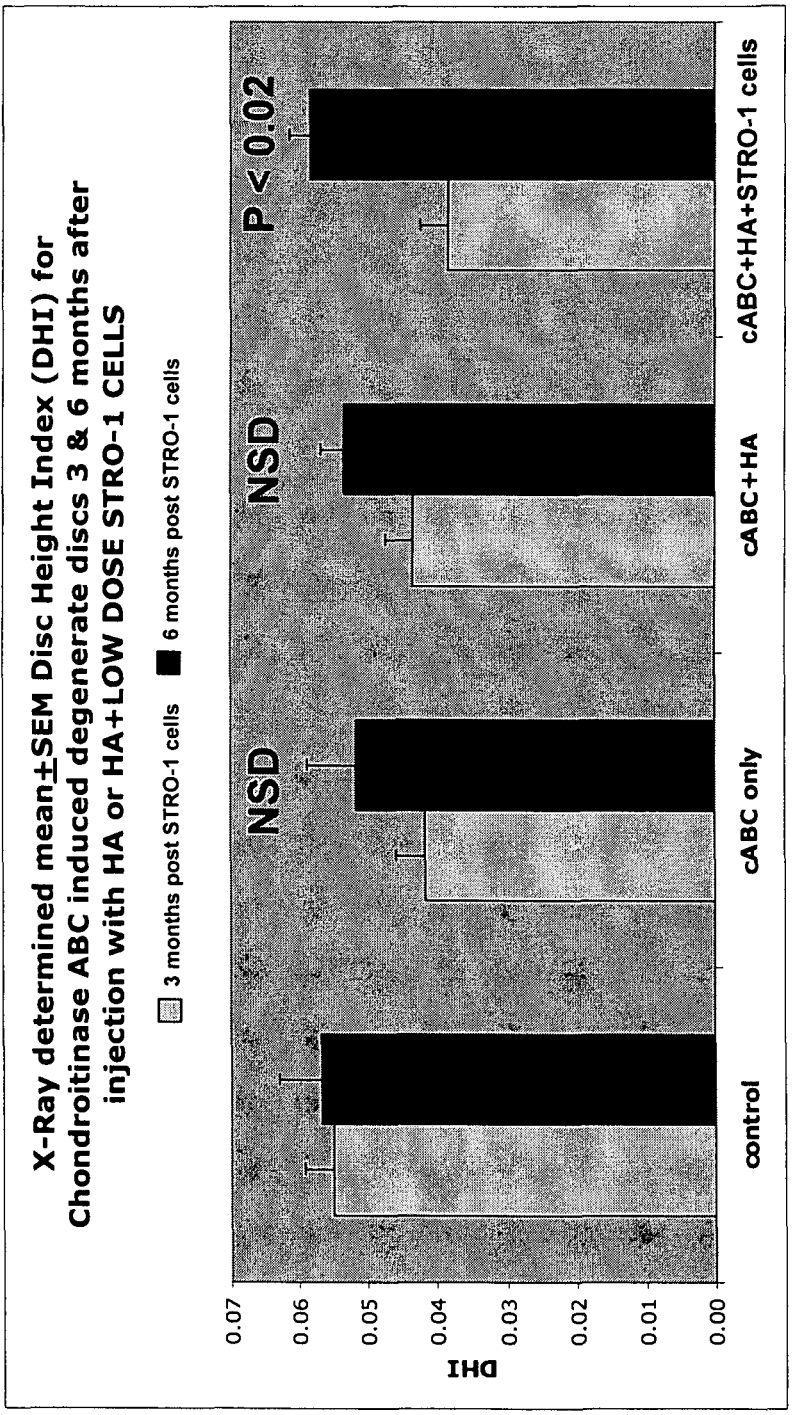
FIG. 12. Radiologically determined Disc Height Index (DHI). A: X-ray determined mean±SEM disc height index (DHI) for chondroitinase ABC induced degenerate discs 3 and 6 months after injection with HA or HA+ low dose STRO-1 cells. B: X-ray determined mean±SEM disc height index (DHI) for chondroitinase ABC induced degenerate discs 3 and 6 months after injection with HA or HA+high dose STRO-1 cells.
Figure 12:
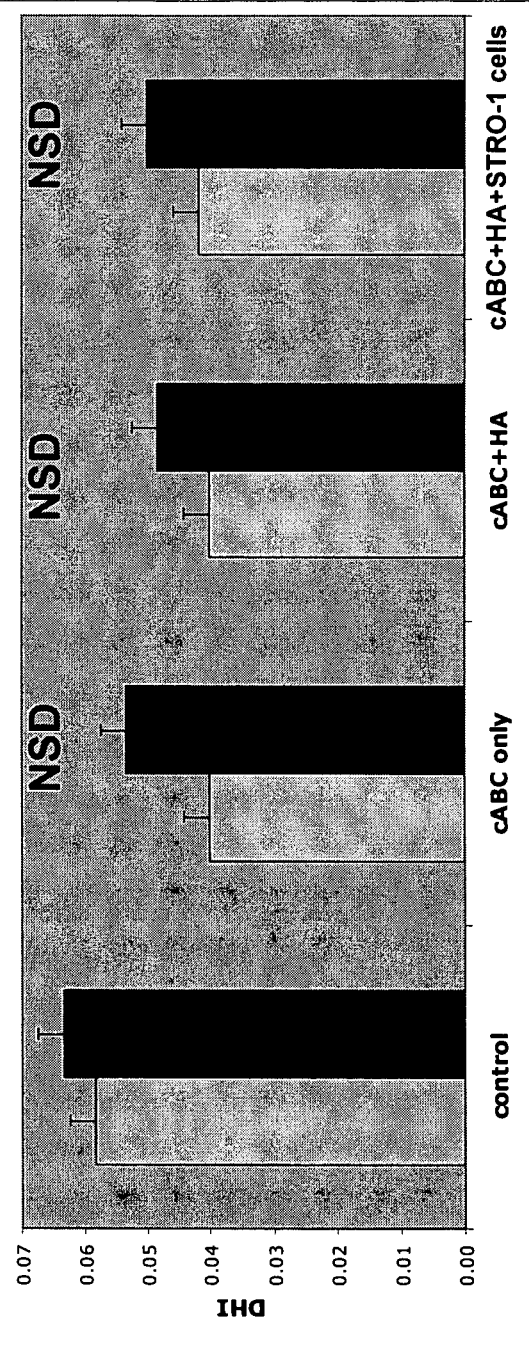

As can be seen from FIG. 12 all injected discs, irrespective of their treatments showed some recovery in their DHI over the 3 months of the post treatment period. However, the largest improvement in DHI was noted for discs injected with low dose STRO-1+ cells where the improvement was shown to be statistically significant (p<0.02). Moreover, the DHI of the low dose STRO-1+ cells injected discs at 6 months were not significantly different from the non-injected control disc DHI mean values (FIG. 12A).

DISCUSSION

The results of the present experiments have shown that intra-discal administration of low dose STRO-1+ cells+HA into degenerate discs improved structural restoration to a greater extent than discs injected with HA. This conclusion was supported by the experimental data generated by three independent assessments of disc integrity and matrix recovery from a baseline degenerative status corresponding to 50% of normal disc height index.

The increase in DHI observed for the low dose STRO-1+ cells injected discs over 6 months may be explained by the deposition within the degenerate discs of a reconstituted extra-cellular matrix. In the healthy spinal column the disc height (DHI) is maintained by the presence within the nucleus pulposus and inner-annulus of high concentrations of PGs and their bound water molecules (2,4). These entities confer a high swelling pressure to the disc that maintains disc height but also allows the disc to recover from deformation after axial compression (2,4). Indeed, the use of chondroitinase-ABC to induce disc degeneration in this animal model relied on the ability of this enzyme to selectively degrade and remove the majority of the PGs from the extra-cellular matrix of the NP and inner AF (28). The histochemical studies using the Alcian Blue dye, which binds to the negatively charged PGs, showed for sections obtained from disc injected with low dose STRO-1+ cells, more intense staining than the cABC alone of cABC+HA injected disc sections confirming the presence of higher concentrations of PGs in these tissues. Examination of these stained sections by both white and fluorescent light microscopy also confirmed the lamella structure of the AF collagen fibril assembly as well as the normalization of hyaline cartilaginous end plate (CEP) morphology. The CEP is a major route of nutrient diffusion into the avascular NP and physical disruption of its structure diminishes the survival of the resident cell.

The concentrations of PGs in the NP, as determined biochemically from the GAG content, were only partly supportive of the histopathology findings. The GAG content of the high and low dose STRO-1+ cells injected NPs at 3 and 6 months were found not to be statistically different from control NP, while the other treated discs were. However, statistical differences between the GAG levels in the cABC+STRO-1+ cells injected discs and the cABC or cABC+HA disc NPs could not be demonstrated suggesting comparable levels of GAGs within the tissues of these groups. As the disc tissues used for the biochemical analysis had been previously fixed in buffered formalin for some months prior to biochemical analysis it is possible that variable amounts of PGs leached out of the matrices over this time. In addition, the collagen and protein covalent crosslinks formed during the formalin fixation process may have impaired adequate macroscopic distinction and dissection of the NP and AF regions of the disc from each other. The dissection was particularly difficult for degenerate discs where the boundary between NP and AF had been lost. Disc AF has a much lower GAG content than NP and therefore sampling errors could have a marked effect on the analytical data (1-4).

Administration of ovine STRO-1+ multipotential cells together with a suitable carrier, such as high molecular weight hyaluronic acid (HA), into the nucleus pulposus of experimentally created degenerate IVDs has been shown in the present experiments to accelerate the regeneration of the disc extracellular matrix as assessed radiographically by the recovery of disc height. This interpretation is based on the assumption that in the loaded spinal column the disc height is maintained by the presence within the NP and inner-annulus of high concentrations of matrix proteoglycans that together with their bound water molecules confer a high swelling pressure to this structure. Indeed, the use of chondroitinase-ABC to induce disc degeneration at the commencement of these experiments relied on the ability of this enzyme to degrade and remove the majority of the proteoglycans from the NP extracellular matrix.

The present results indicated that the recovery of discs from the degenerative state induced by earlier injection of cABC was more sustained with the lower dose of $(0.5 \times 10^6)$ than with the higher dose $(4.0 \times 10^6)$ of STRO-1$^+$ cells. A possible explanation for this observation could be related to the poor nutritional supply to the NP of the disc that is dependent on the exchange of $O_2/CO_2$ and metabolites between the blood vessels beneath to the CEP (1, 2). As already mentioned even minor disruption of the interface between the NP the CEP and the subchondral blood supply of the vertebrae, as was seen to occur in the degenerate discs would be expected to impair nutrition to the NP. This nutritional deficiency could present an upper limit to the number of injected STRO-1$^+$ cells that could survive in this oxygen-deprived environment thereby resulting in loss of their viability and thus therapeutic benefits.

The therapeutic mechanisms responsible for the recovery of disc integrity in this animal model following administration of low dose STRO-1$^+$ multipotential cells have yet to be resolved. However, it is possible that anti-inflammatory cytokines and growth factors, released by the STRO-1$^+$ multipotential cells within the degenerate disc space would modulate the pro-catabolic and anabolic suppressive effects mediated by cytokines and other noxious factors released by the resident disc cells in response to biochemical and biomechanical injury. These STRO-1$^+$ multipotential cells derived paracrine factors could also support the normal physiological anabolic response of resident disc cells to the depletion of PGs from their extra-cellular environment as was occasionally seen in some of the non-STRO-1$^+$ cells injected discs. On the other hand it is possible that some STRO-1$^+$ multipotential cells may engraft within the degenerate matrix and undergo differentiation into NP chondrocytes or other disc cells.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

1. Fraser R D, Osti O L, Vernon-Roberts B. (1993) Intervertebral disc degeneration. Ear. Spine J. 1, 205-213
2. Vernon Roberts B. (1988) Pathology of the intervertebral disc. In Biology of the Intervertebral disc Vol II. Ed. P. Ghosh, Boca Raton, CRC Press, pp 73-120.
3. Osti O. L., Vernon-Roberts B., Moore R. et al (1992) Annulus tears and intervertebral disc degeneration in the human lumbar spine: a post-mortem study of 135 discs. J. Bone & Jt. Surg [Br], 74, 678-682.
4. Pearce R J, Grimmer B J, Adams M E (1987) Degeneration and the chemical composition of the human intervertebral disc. J Orthop Res. 5, 198-205
5. Hadler N M (1986) The Australian and New Zealand experiences with arm-pain and back-ache in the work-place Med. J. Aust. 144, 191.
6. Frymoyer J W and Cats-Baril W I (1991) An overview of the incidence and costs of low back pain. Orthop. Clin. North. Am. 22, 263-271.
7. Freemont A J, Peacock T E, Goupille P, Hoyland J A, O'Brien J, Jayson M I V (1997) Nerve in-growth into the diseased intervertebral disc in chronic back pain. Lancet, 350, 178-181.
8. Lam K S, Carlin D, Mulholland R C (2000) Lumbar disc high intensity zone: the value and significance of provocative discography in the determination of the dicogenic pain source. Eur. Spine. J. 9, 36-41.
9. Barrick W T, Schofferman J A, Reynolds J B, Goldthwaite N D, McKeehen M, Feaney, D, White A H (2000) Anterior lumbar spinal fusion improves discogenic pain at levels of prior posterolateral fusion. Spine, 25, 853-7.
10. Luoma, K., Riihimaki H, Luukkonen R et al (2000) Low back pain in relation to lumbar disc degeneration. Spine, 15, 487-92.
11. Anderson, J A D (1987) Back pain and occupation. In Jayson M. I. V. (ed) The lumbar spine in back pain. 3rd ed. London, Churchill Livingstone 2-36.
12. Moore R. J., Crotti T N, Osti O. L., Fraser R D, Vernon-Roberts B. (1999) Osteoarthritis of the facet joints resulting from anular rim lesions of sheep lumbar discs. Spine, 24, 519-525.
13. Bogduk N, Tynan W, Wilson A S (1981) The nerve supply to the human intervertebral disc. J. Anat., 132, 39-56.
14. Malinsky J (1959) The ontogenetic development of nerve terminations in the intervertebral discs of man. Acta. Anat. 38, 96-113.
15. Yoshizawa H, O'Brien J P, Smith W T, Trumper M (1980) The neuropathology of intervertebral discs removed for low back pain. J. Path. 132, 95-104.
16. Taylor T K F, Ghosh P, Braund K G, Sutherland J M and Sherwood A A: The effect of spinal fusion on intervertebral disc composition: An experimental study. J. Surg. Res. 21(2): 91-104, 1976).
17. Takegami K, Masuda K, An H, Chiba K et al (1999) Osteogenic protein-1 is most effective in stimulating nucleus pulposus and annulus fibrosus cells to repair their matrix after chondroitrinase ABC induced chemonucleolysis. Trans. Orthop. Res. Soc. 24, 201-202.
18. Ganey T, Meisel H J, Hutton W, Alasevic O, Libera J. Pre-clinical model for assessing autologous disc chondrocytes in intervertebral disc repair. Spine 28:2609-20; 2003.
19. Gerber B E. Five to six years follow up results after biological disc repair by reimplantation of cultured autologous disc tissue. Proceedings of The International Cartilage Repair Society Annual Scientific Meeting, Toronto, Canada 2002.
20. Zannettino et al. (1998) Blood 92:2613-2628.
21. Gronthos et al. (2003) Journal of Cell Science 116: 827-1835.
22. Gronthos et al. (1995). Blood 85:929-940.

23. Sakai D et al (2005). Differentiation of mesenchymal stem cells transplanted to a rabbit degenerative disc model: potential and limitations for stem cell therapy in disc regeneration. Spine 30:2379-87.
24. Masuda K, Aota Y, Muehleman C, Imai Y, Okuma M, Thonar E J, Andersson G B, An H S. A novel rabbit model of mild reproducible disc degeneration by an annulus needle puncture: Correlation between the degree of disc injury and radiological and histological appearances of disc degeneration. Spine 30:5-14, 2004
25. Pfirrmann C W A et al Spine 26:1873-1878, 2001.
26. Gries N C, Berlemann U, Moore R J, Vernon-Roberts B. Early histological changes in lower lumbar discs and facet joints and their correlation. Eur. Spine J. 9:23-29, 2000.
27. Burkhardt D, Hwa S-Y and Ghosh P. A novel microassay for the quantitation of the sulfated glycosaminoglycan content of histological sections: Its application to determine the effects of Diacerhein on cartilage in an ovine model of osteoarthritis. Osteoarthritis Cartilage 9: 238-247, 2001.
28. Sugimura T, Kato F, Mimatsu K, Takenaka O, Iwata H. Experimental chemonucleolysis with chondroitinase ABC in monkeys. Spine 21: 161-5, 1996.

The invention claimed is:

1. A method for treating a degenerated intervertebral disc in a subject, the method comprising administering to the degenerated intervertebral disc a population of cells which has been enriched for STRO-1$^{bright}$ multipotential cells and/or progeny cells thereof, wherein administering the cells causes regeneration and/or repair of the degenerated intervertebral disc, and wherein the STRO-1$^{bright}$ multipotential cells and/or progeny cells thereof are administered into the nucleus pulposus of the degenerated intervertebral disc.

2. The method according to claim 1 wherein the STRO-1$^{bright}$ multipotential cells are also positive for TNAP+ (STRO-3), VCAM-1+, THY-1+, STRO-2+, CD45+, CD146+, 3G5+, or any combination thereof.

3. The method according to claim 1 wherein the STRO-1$^{bright}$ multipotential cells are derived from an allogeneic source.

4. The method according to claim 1 which further comprises administering to the degenerated intervertebral disc a glycosaminoglycan (GAG).

5. The method according to claim 4 wherein the GAG is selected from the group consisting of hyaluronic acid (HA), chondroitan sulfate, dermatan sulfate, keratan sulfate, heparin, heparin sulfate, and galactosaminoglycuronglycan sulfate (GGGS).

6. The method according to claim 1 wherein the subject has a spinal condition characterized by degeneration of the intervertebral disc.

7. The method according to claim 6 wherein the spinal condition is low back pain, age-related changes of the intervertebral disc, or spondylolysis.

* * * * *